US011447741B2

(12) United States Patent
Beck et al.

(10) Patent No.: US 11,447,741 B2
(45) Date of Patent: Sep. 20, 2022

(54) *LACTOBACILLUS PLANTARUM* STRAIN ATG-K2, ATG-K6 OR ATG-K8, AND COMPOSITION FOR PREVENTING OR TREATING VAGINITIS COMPRISING SAME

(71) Applicant: ATOGEN CO., LTD, Daejeon (KR)

(72) Inventors: Bo Ram Beck, Daejeon (KR); Ji Hee Kang, Daejeon (KR); Gun Seok Park, Daejeon (KR); Sung Hoon Im, Daejeon (KR); Do Yeun Jeong, Daejeon (KR); Yong Hyun Lee, Daejeon (KR)

(73) Assignee: ATOGEN CO., LTD, Daejeon (KR)

( * ) Notice: Subject to any disclaimer, the term of this patent is extended or adjusted under 35 U.S.C. 154(b) by 0 days.

(21) Appl. No.: 17/051,007

(22) PCT Filed: Jun. 10, 2019

(86) PCT No.: PCT/KR2019/006936
§ 371 (c)(1),
(2) Date: Oct. 27, 2020

(87) PCT Pub. No.: WO2020/075949
PCT Pub. Date: Apr. 16, 2020

(65) Prior Publication Data
US 2021/0324326 A1   Oct. 21, 2021

(30) Foreign Application Priority Data
Oct. 12, 2018 (KR) .......................... 10-2018-0121634

(51) Int. Cl.
| | |
|---|---|
| *A61K 35/747* | (2015.01) |
| *A61K 35/74* | (2015.01) |
| *A61K 35/00* | (2006.01) |
| *C12N 1/20* | (2006.01) |
| *A61P 15/02* | (2006.01) |
| *C12R 1/25* | (2006.01) |

(52) U.S. Cl.
CPC .............. *C12N 1/205* (2021.05); *A61K 35/74* (2013.01); *A61K 35/747* (2013.01); *A61P 15/02* (2018.01); *A23Y 2220/67* (2013.01); *A61K 2035/115* (2013.01); *C12R 2001/25* (2021.05)

(58) Field of Classification Search
None
See application file for complete search history.

(56) References Cited

U.S. PATENT DOCUMENTS

2019/0000894 A1* 1/2019 Malanchin ........... A61K 35/745

FOREIGN PATENT DOCUMENTS

| KR | 10-1098241 B1 | 12/2011 |
| KR | 10-1750468 B1 | 6/2017 |
| KR | 10-1784847 B1 | 10/2017 |
| KR | 10-1860513 B1 | 5/2018 |
| KR | 10-2018-0094926 A | 8/2018 |
| KR | 10-1930438 B1 | 12/2018 |

OTHER PUBLICATIONS

Park.G.-S. et al., "Lactobacillus plantarum strain ATG-K2 chromosome, complete genome", GenBank: CP032460.1, Sep. 26, 2018, 1 page.
Park.G.-S. et al., "Lactobacillus plantarum strain ATC-K6 chromosome, complete genome", GenBank: P032464.1, Sep. 26, 2018, 1 page.
Park.G.-S. et al., "Lactobacillus plantarum strain ATG-K8 chromosome, complete genome", GenBank: CP032466.1, Sep. 26, 2018, 1 page.
Bo Ram Beck et al., "Whole Genome Analysis of Lactobacillus plantarum strains Isolated from Kimchi and Determination of Probiotic Properties to Treat Mucosal Infections by Candida albicans and Gardnerella vaginalis", Frontiers in Microbiology, Mar. 6, 2019, pp. 1-13, vol. 10, Article 433.
Belma Aslim et al., "Factors Influencing Autoaggregation and Aggregation of *Lactobacillus delbrueckii* Subsp. *bulgaricus* Isolated from Handmade Yogurt", Journal of Food Protection, 2007, pp. 223-227, vol. 70, No. 1.
Maire Begley et al., "Bile Salt Hydrolase Activity in Probiotics", Applied and Environmental Microbiology, 2006, pp. 1729-1738, vol. 72, No. 3.
Sara Bover-Cid et al., "Improved screening procedure for biogenic amine production by lactic acid bacteria", International Journal of Food Microbiology, 1999, pp. 33-41, vol. 53.
Michael P. Dashkevicz et al., "Development of a Differential Medium for Bile Salt Hydrolase-Active *Lactobacillus* spp.", Applied Environmental Microbiology, Jan. 1989, pp. 11-16, vol. 55, No. 1.
Maaike C. De Vries et al., "Lactobacillus plantarum—Survival, Functional and Potential Probiotic Properties in the Human Intestinal Tract", International Dairy Journal, 2006, pp. 1018-1028, 16.
"Guidance on the assessment of bacterial susceptibility to antimicrobials of human and veterinary importance, EFSA Panel on Additives and Products or Substances used in Animal Feed (FEEDAP)", EFSA Journal, 2012, 2740, 10(6), 10 pages.

(Continued)

*Primary Examiner* — Sarvamangala Devi
(74) *Attorney, Agent, or Firm* — Sughrue Mion, PLLC

(57) ABSTRACT

A novel *Lactobacillus plantarum* strain ATG-K2, ATG-K6 or ATG-K8 and a composition for the prevention or treatment of vaginitis containing the same are proposed. The *Lactobacillus plantarum* strain ATG-K2, ATG-K6 or ATG-K8 has excellent antimicrobial effects against various pathogenic strains as well as *Candida albicans* and *Gardnerella vaginalis*, which are vaginitis pathogens, and thus can be easily used as a composition for the treatment of bacterial vaginosis, vaginal candidiasis, etc., or as a functional health food for the prevention or amelioration of these diseases.

7 Claims, 16 Drawing Sheets

Specification includes a Sequence Listing.

(56) References Cited

OTHER PUBLICATIONS

Mari Egan, M.D. et al., "Vaginitis: Case Reports and Brief Review", AIDS Patient Care and STDS, 2002, pp. 367-373, vol. 16, No. 8.
Ceri A. Fielding et al., "IL-6 Regulates Neutrophil Trafficking during Acute Inflammation via STAT3", The Journal of Immunology, 2008, pp. 2189-2195, 181.
David F. Fiorentino et al., "IL-10 Inhibits Cytokine Production by Activated Macrophages", The Journal of Immunology, Dec. 1, 1991, pp. 3815-3822, vol. 147.
Pauline S. Handley et al., "A Comparison of the Adhesion, Coaggregation and Cell-surface Hydrophobicity Properties of Fibrillary and Fimbriate Strains of Streptococcus salivarius", Journal of General Microbiology, 1987, pp. 3207-3217, vol. 133.
Jacqueline A. McGroarty et al., "Hydrogen Peroxide Production by Lactobacillus Species: Correlation With Susceptibility to the Spermicidal Compound Nonoxynol-9", The Journal of Infectious Diseases, Jun. 1992, pp. 1142-1144, vol. 165.
Marianne Morris et al., "Bacterial vaginosis: a public health review", British Journal Obstetrics and Gynaecology, May 2001, pp. 439-450, vol. 108.
Jurgen Scheller et al., "The pro- and anti-inflammatory properties of the cytokine interleukin-6", Biochimica Biophysica Acta, 2011, pp. 878-888, vol. 1813, No. 5.
Jack D. Sobel, M.D., "Vaginitis", The New England Journal of Medicine, Dec. 25, 1997, pp. 1896-1903, vol. 337, No. 26.
Nikola L. Vujanovic, "Role of TNF superfamily ligands in innate immunity", Immunol Res, 2011, pp. 159-174, vol. 50.
International Search Report for PCT/KR2019/006936, dated Sep. 24, 2019.

* cited by examiner

[FIG. 1]

| | | |
|---|---|---|
| ATG-K2 | CATCAGACTTTCGTCCATTGTGGAAGATTCCCTACTGCTGCCTCCCGTAGGAGTTTGGGC | 1138 |
| ATG-K6 | CATCAGACTTTCGTCCATTGTGGAAGATTCCCTACTGCTGCCTCCCGTAGGAGTTTGGGC | 1140 |
| ATG-K8 | CATCAGACTTTCGTCCATTGTGGAAGATTCCCTACTGCTGCCTCCCGTAGGAGTTTGGGC | 1140 |
| | ************************************************************ | |
| ATG-K2 | CGTGTCTCAGTCCCAATGTGGCCGATTACCCTCTCAGGTCGGCTACGTATCATTGCCATG | 1198 |
| ATG-K6 | CGTGTCTCAGTCCCAATGTGGCCGATTACCCTCTCAGGTCGGCTACGTATCATTGCCATG | 1200 |
| ATG-K8 | CGTGTCTCAGTCCCAATGTGGCCGATTACCCTCTCAGGTCGGCTACGTATCATTGCCATG | 1200 |
| | ************************************************************ | |
| ATG-K2 | GTGAGCCGTTACCTCACCATCTAGCTAATACGCCGCGGGACCATCCAAAAGTGATAGCCG | 1258 |
| ATG-K6 | GTGAGCCGTTACCCCACCATCTAGCTAATACGCCGCGGGACCATCCAAAAGTGATAGCCG | 1260 |
| ATG-K8 | GTGAGCCGTTACCCCACCATCTAGCTAATACGCCGCGGGACCATCCAAAAGTGATAGCCG | 1260 |
| | ************ ************************************************ | |
| ATG-K2 | AAGCCATCTTTCAAACTCGGACCATGCGGTCCAAGTTGTTATGCGGTATTAGCATCTGTT | 1318 |
| ATG-K6 | AAGCCATCTTTCAACCTCGGACCATGCGGTCCAAGTTGTTATGCGGTATTAGCATCTGTT | 1320 |
| ATG-K8 | AAGCCATCTTTCAAACTCGGACCATGCGGTCCAAGTTGTTATGCGGTATTAGCATCTGTT | 1320 |
| | ************* *********************************************** | |
| ATG-K2 | TCCAGGTGTTATCCCCCGCTTCTGGGCAGGTTTCCCACGTGTTACTCACCAGTTCGCCAC | 1378 |
| ATG-K6 | TCCAGGTGTTATCCCCCGCTTCTGGGCAGGTTTCCCACGTGTTACTCACCAGTTCGCCAC | 1380 |
| ATG-K8 | TCCAGGTGTTATCCCCCGCTTCTGGGCAGGTTTCCCACGTGTTACTCACCAGTTCGCCAC | 1380 |
| | ************************************************************ | |

[FIG. 2]
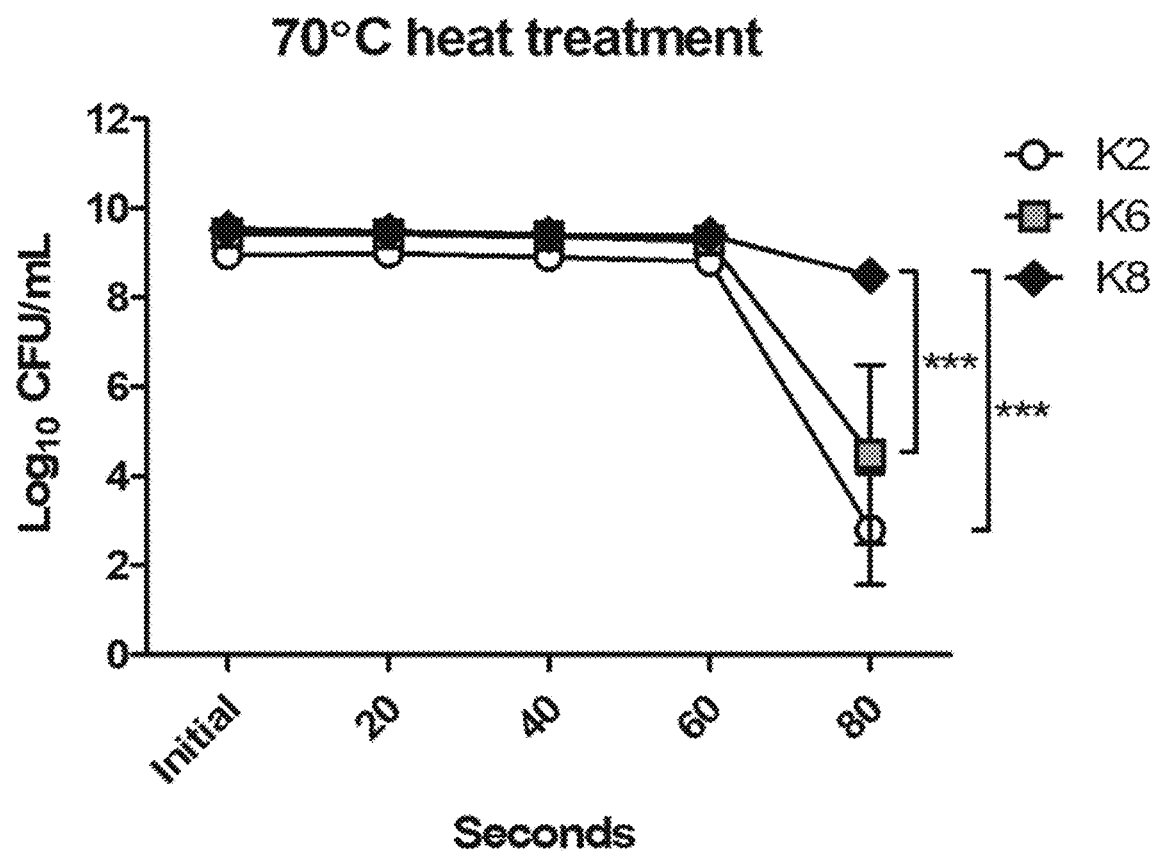

[FIG. 3A]
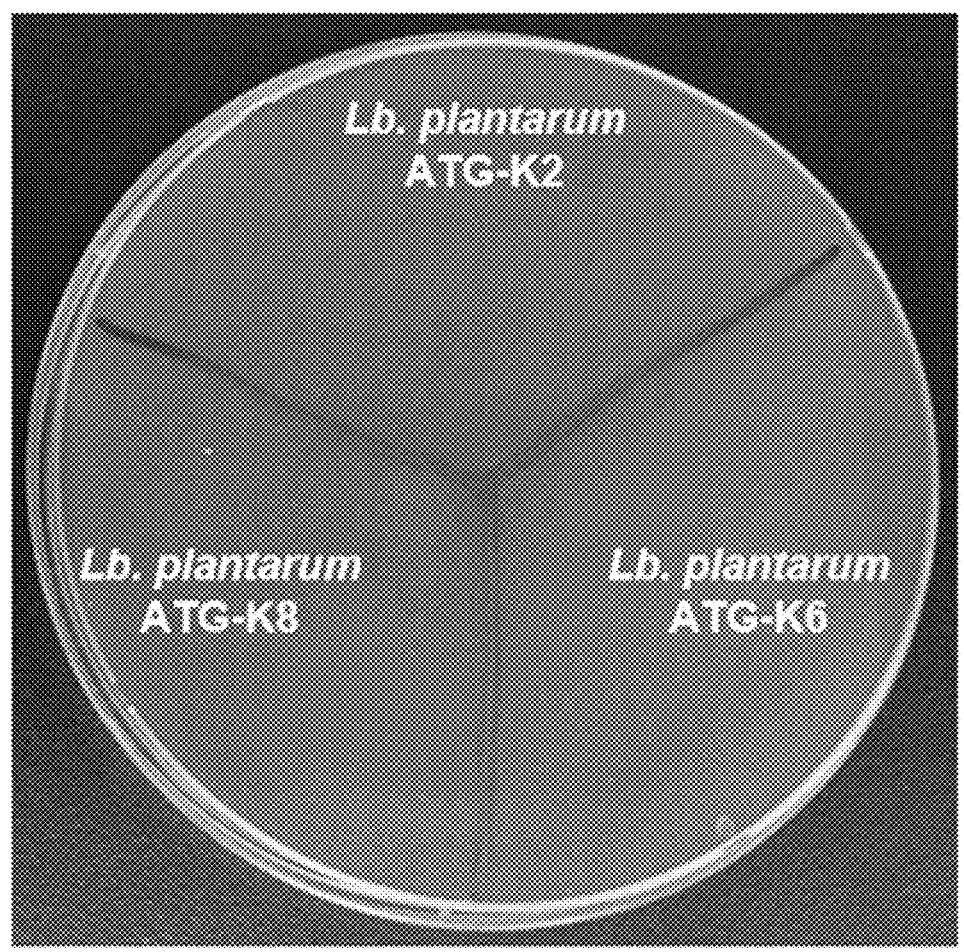

[FIG. 3B]
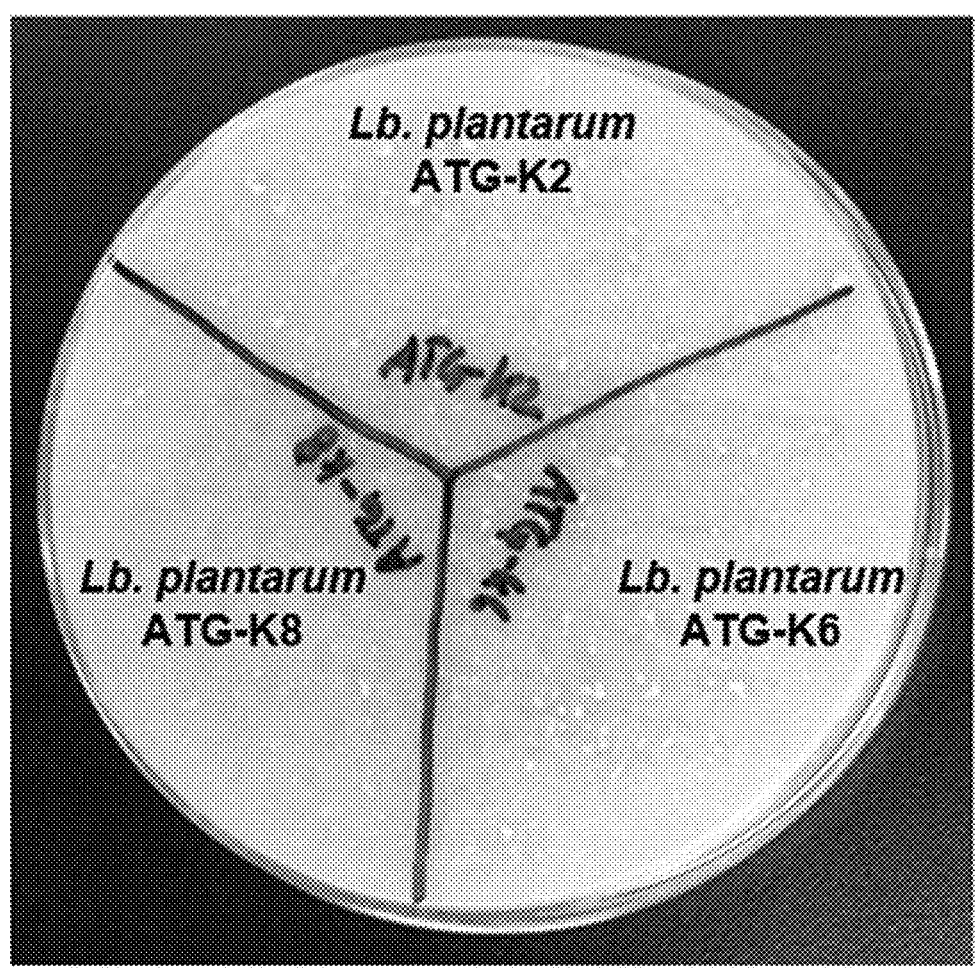

[FIG. 4A]
A
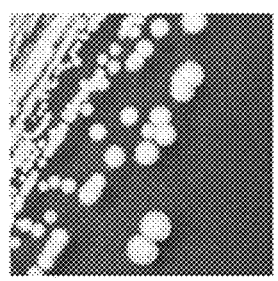 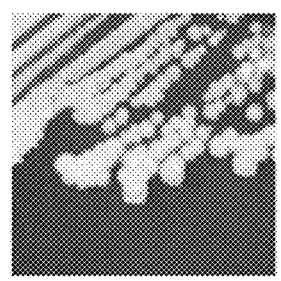 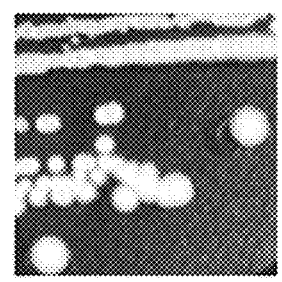
BSH
K2　　K6　　K8
[FIG. 4B]
B
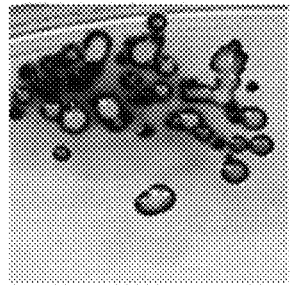 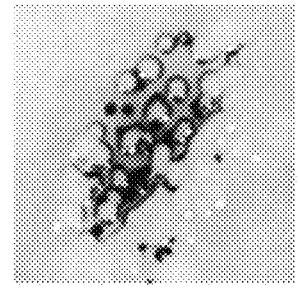 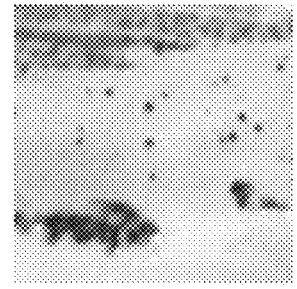
$H_2O_2$
K2　　K6　　K8

[FIG. 4C]
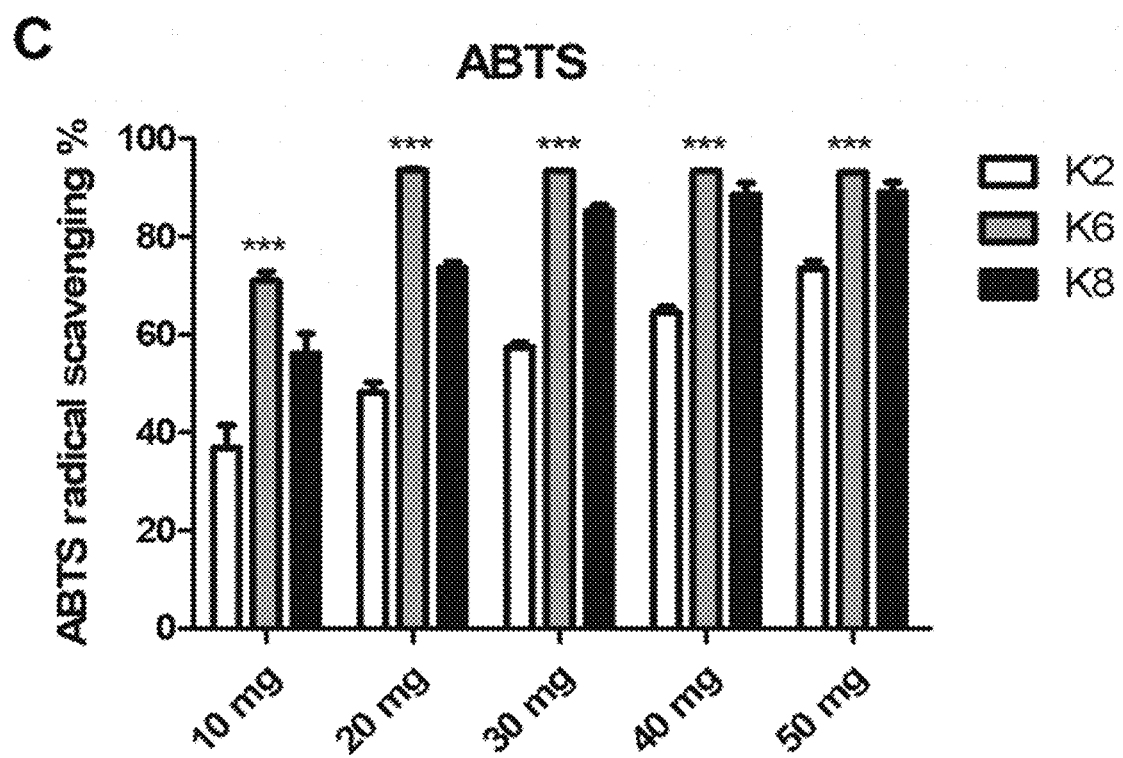

[FIG. 5A]
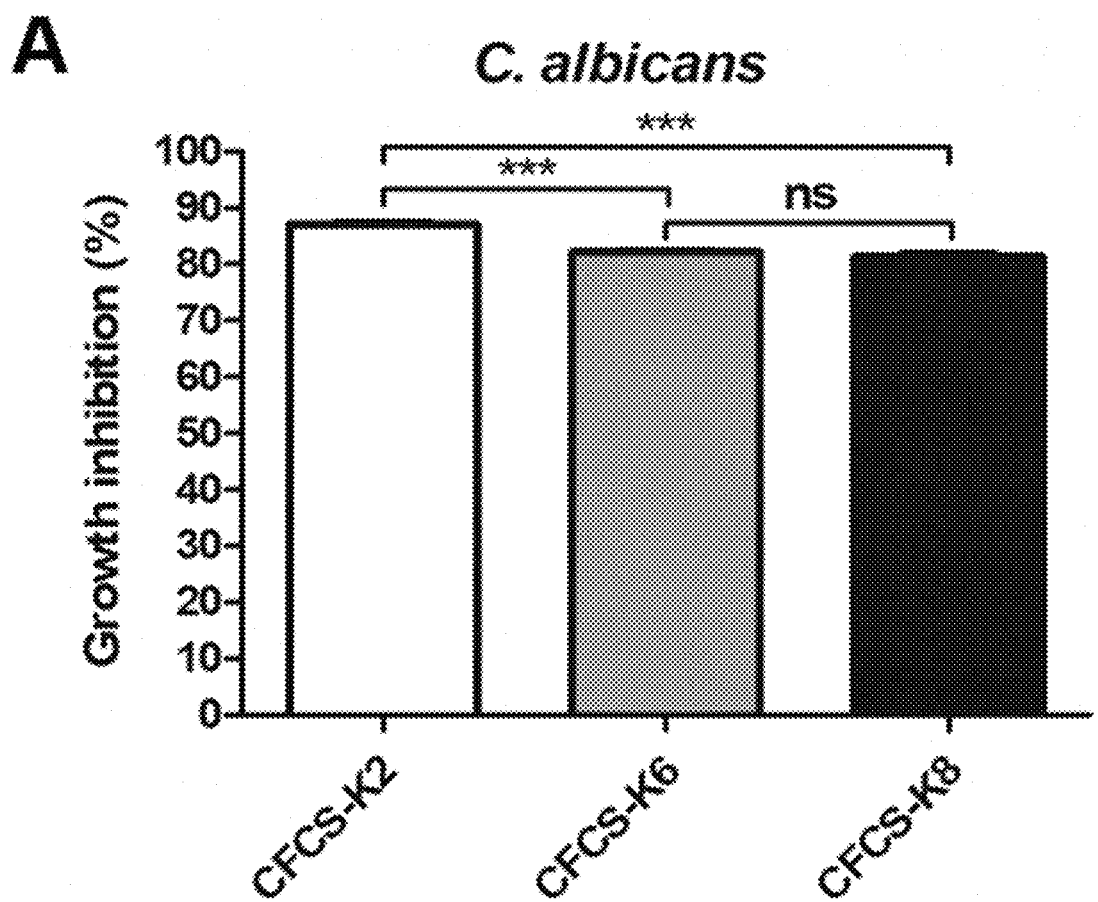

[FIG. 5B]
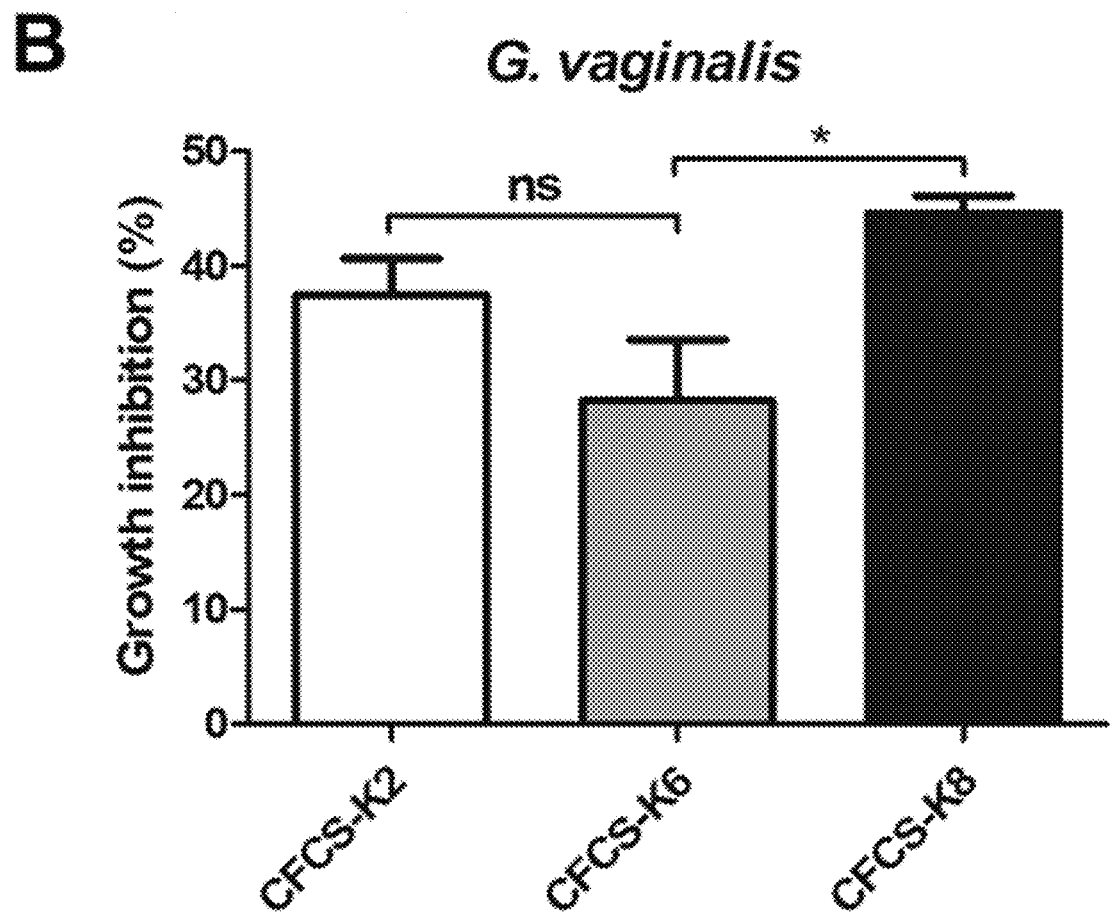

[FIG. 5C]
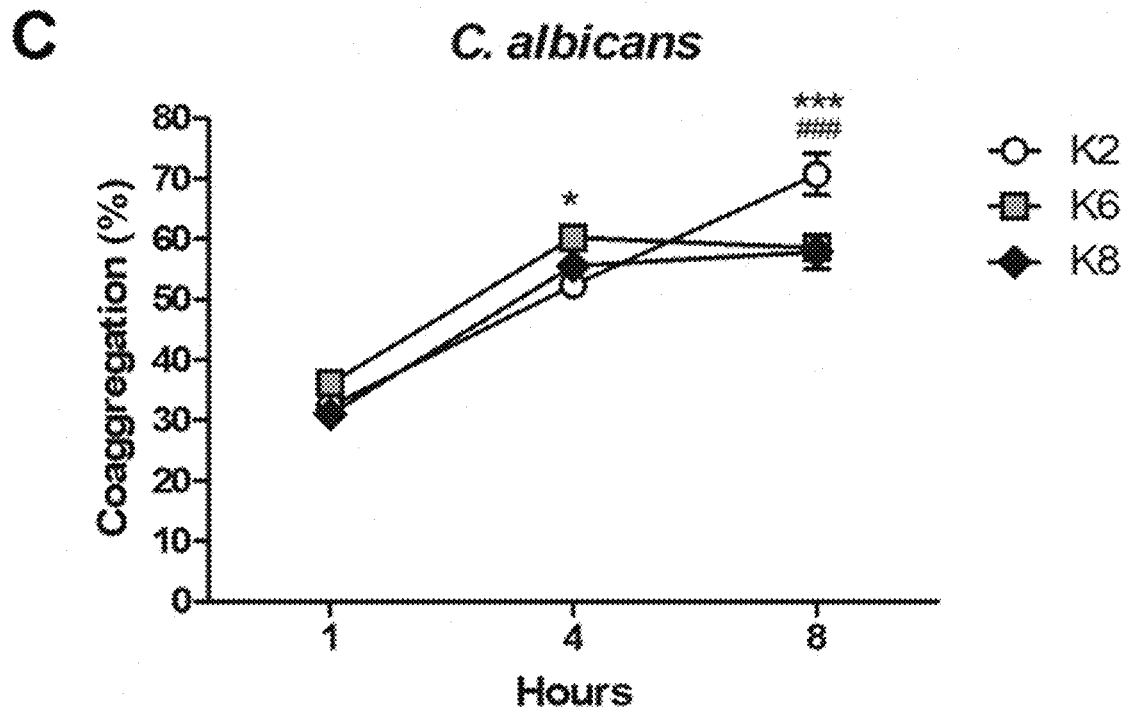
[FIG. 5D]
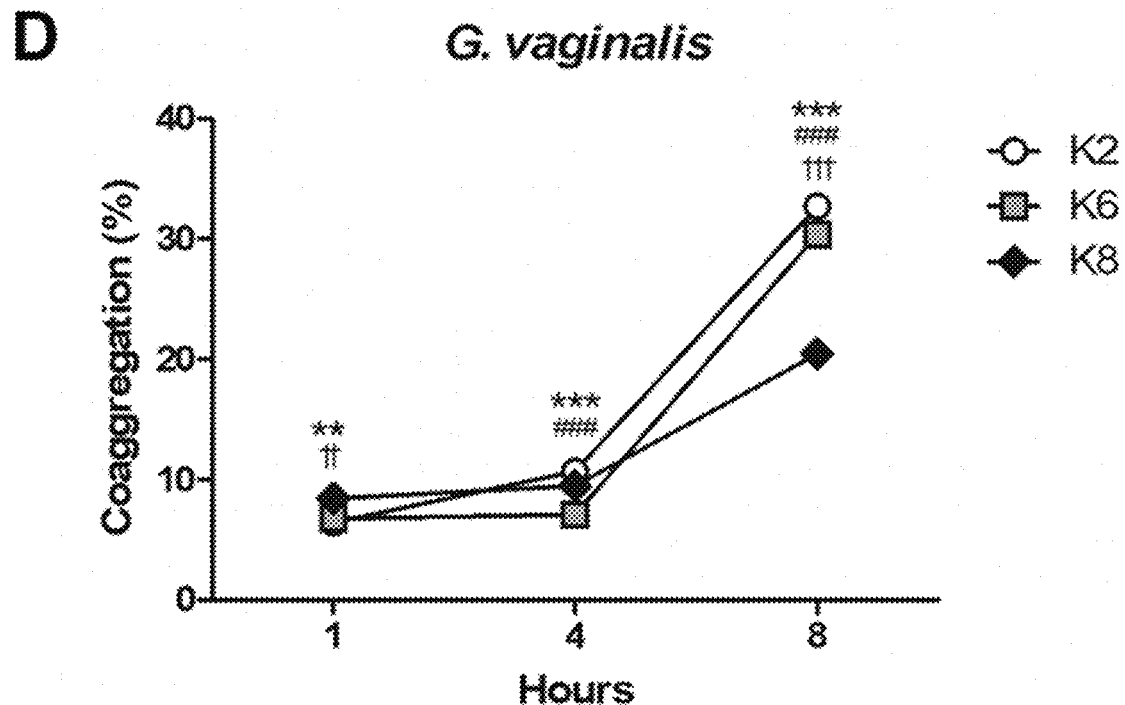

[FIG. 6A]
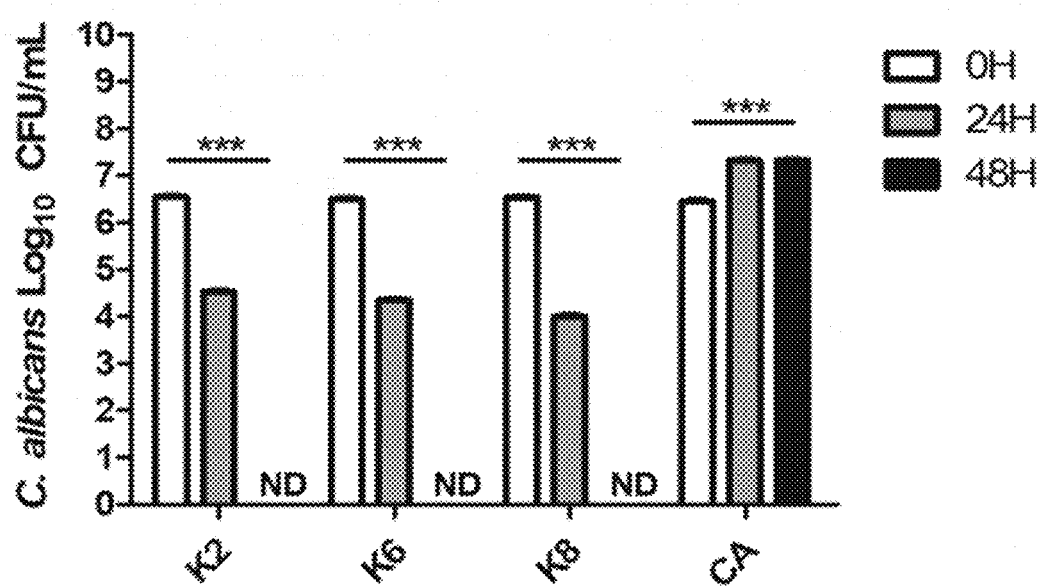

[FIG. 6B]
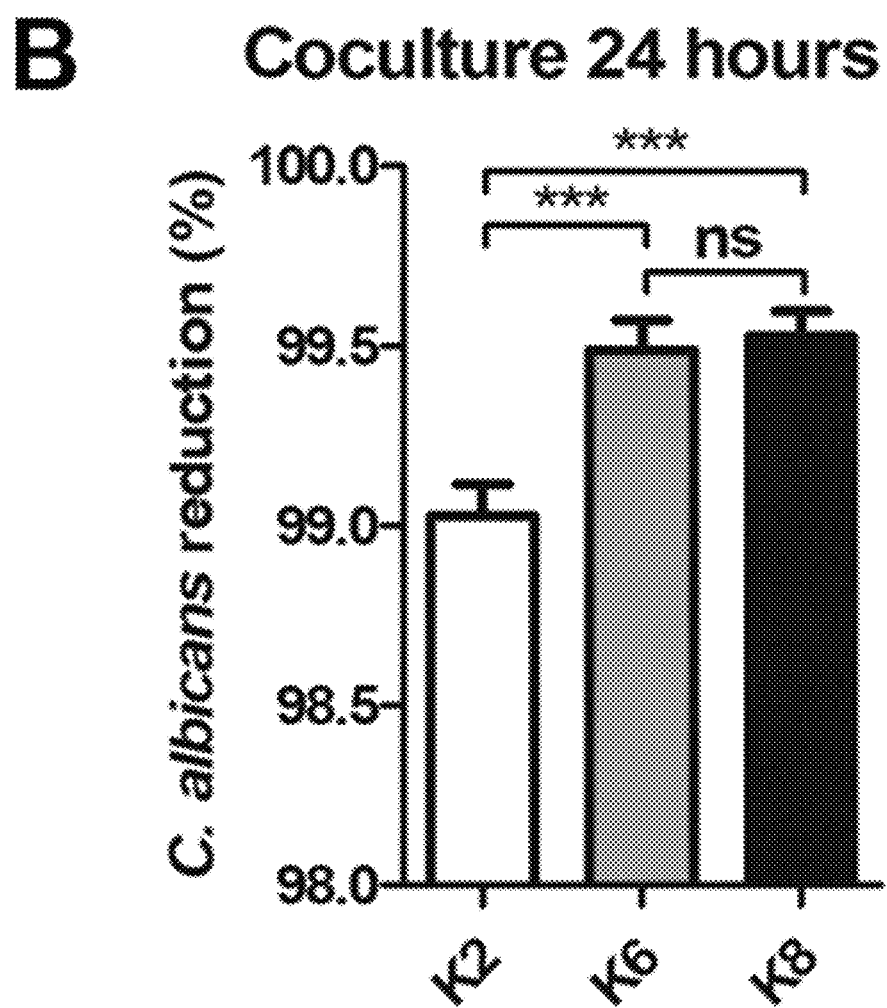

[FIG. 6C]
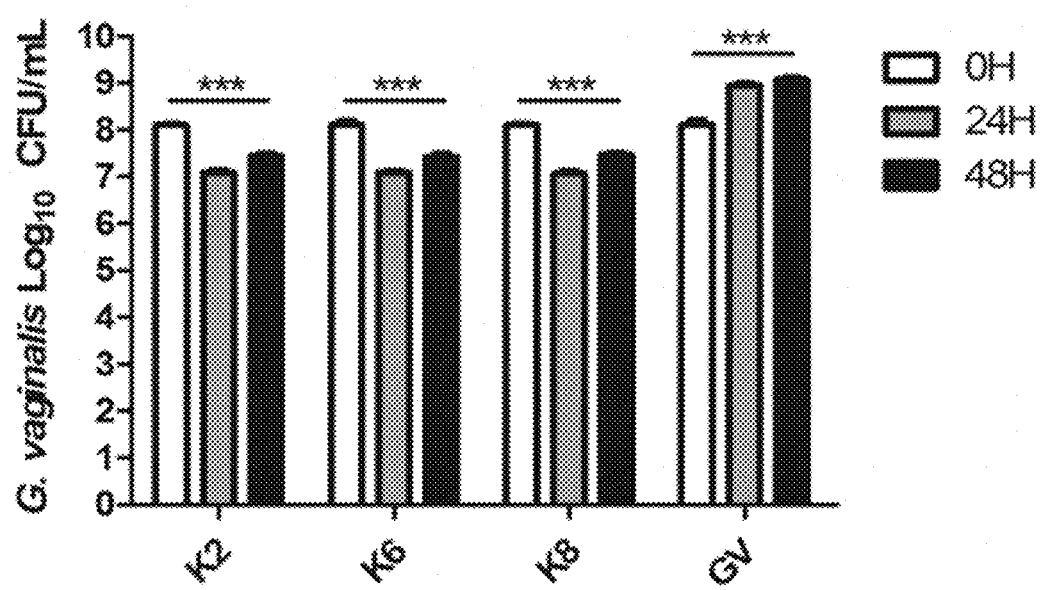

[FIG. 6D]
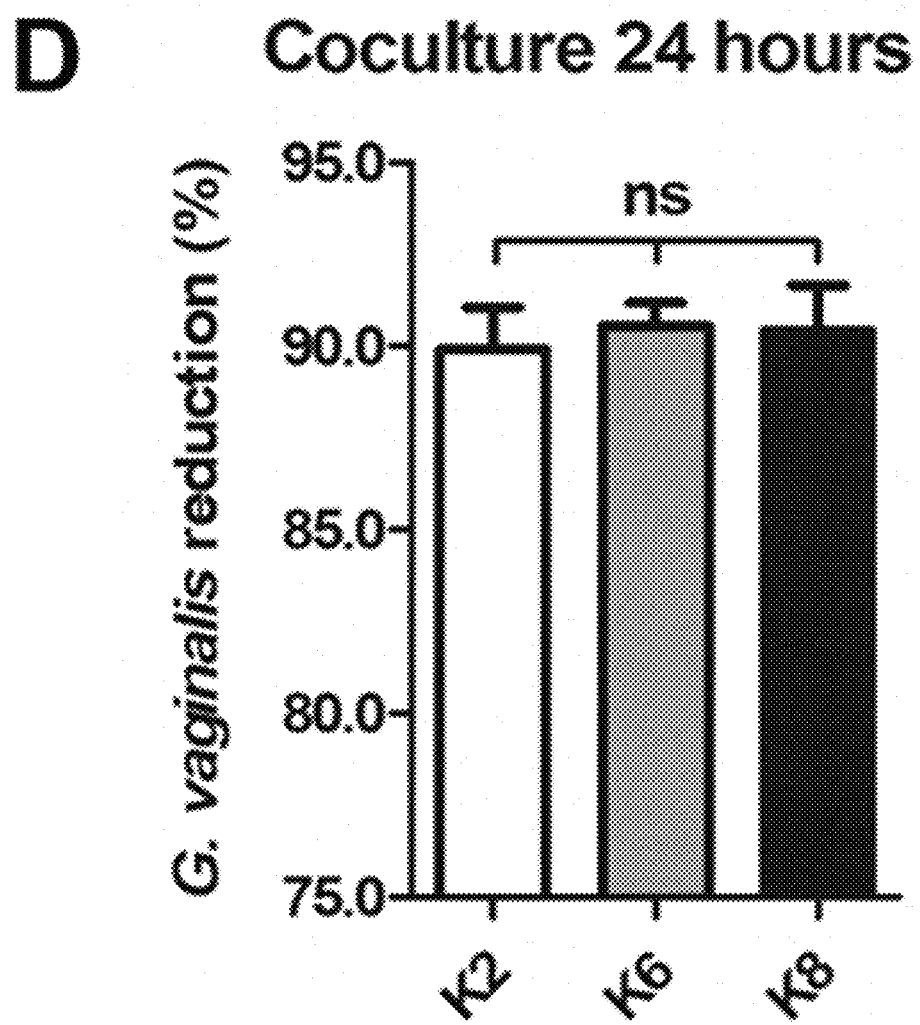

[FIG. 7A]
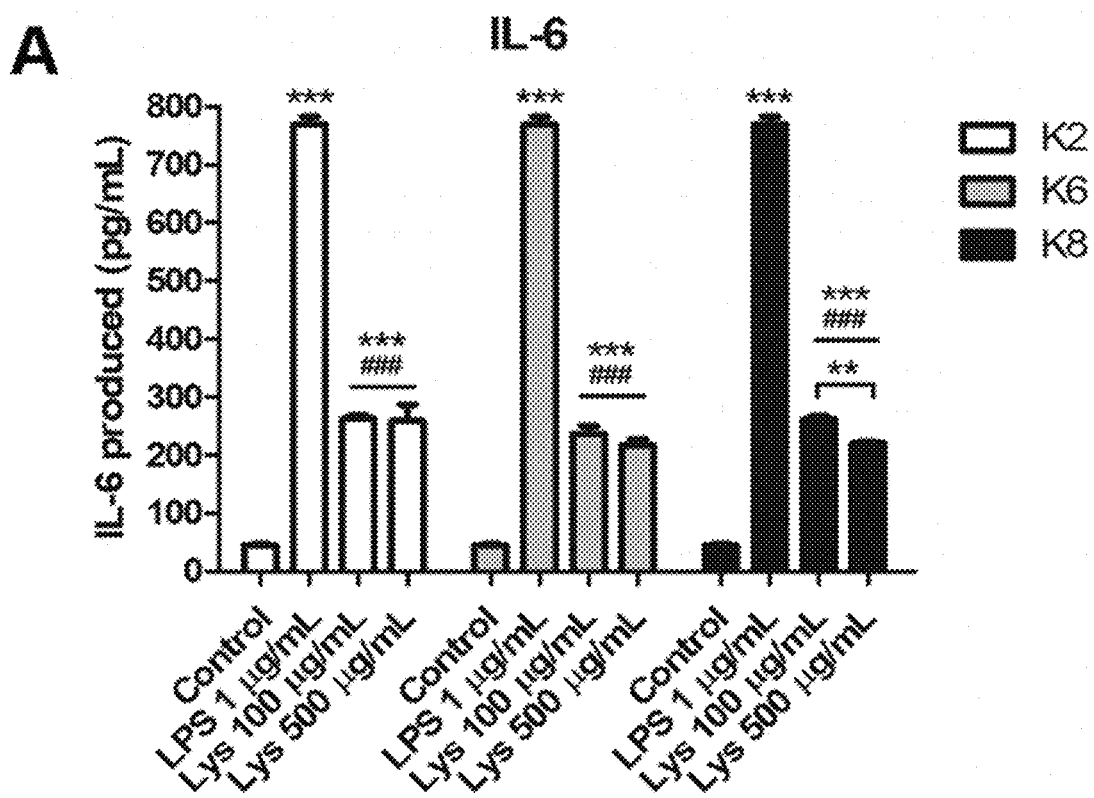

[FIG. 7B]
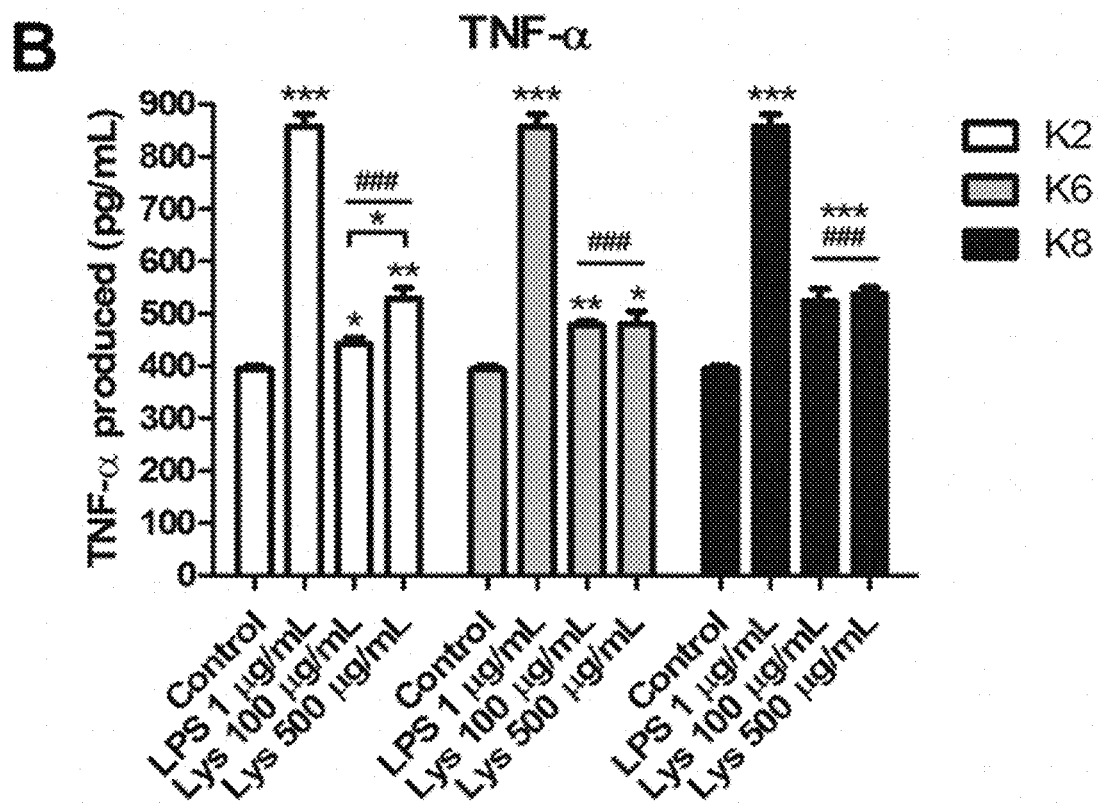

[FIG. 8]
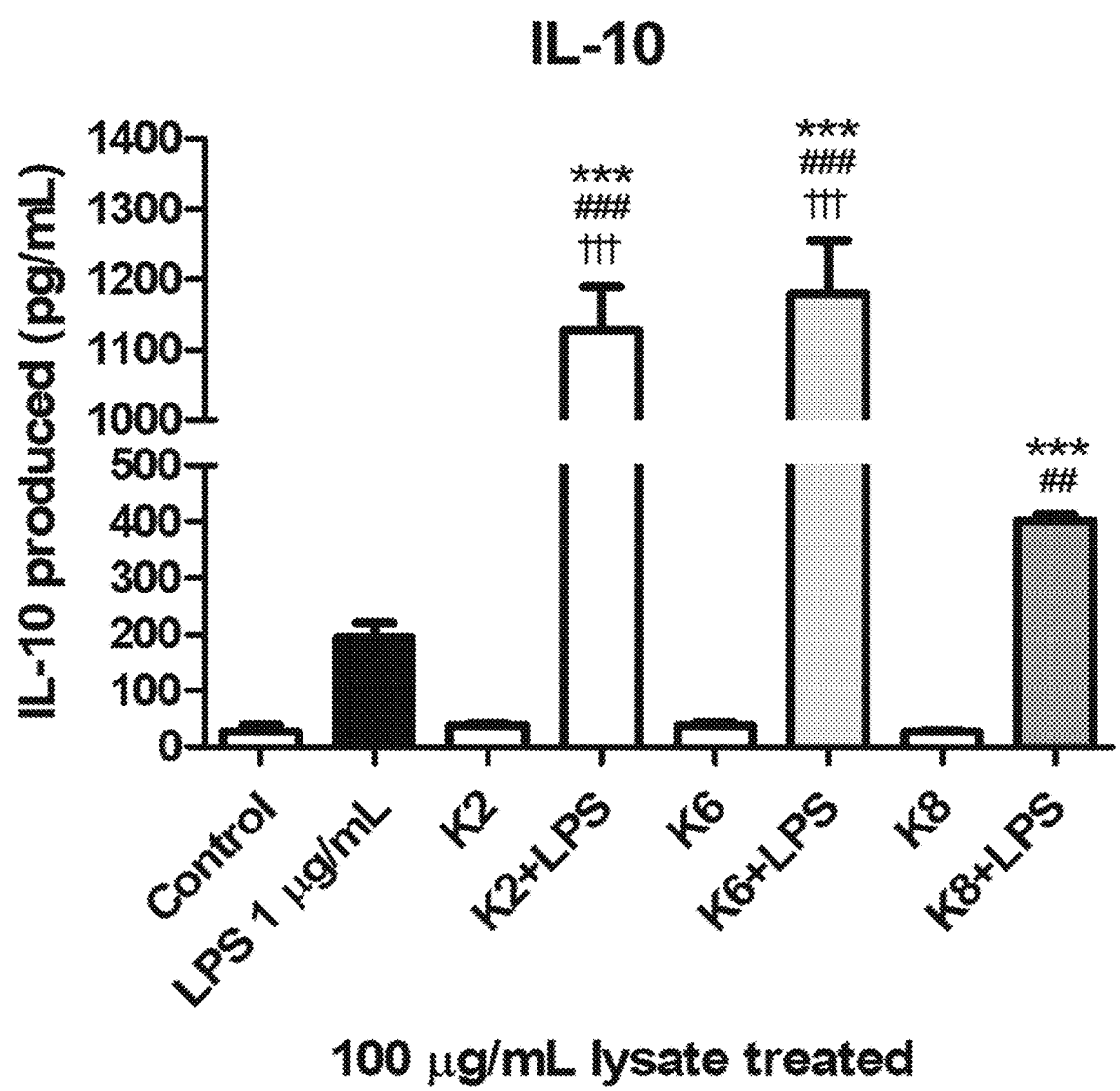

SEQUENCE LISTING

```
<160> NUMBER OF SEQ ID NOS: 7

<210> SEQ ID NO 1
<211> LENGTH: 1482
<212> TYPE: DNA
<213> ORGANISM: Unknown
<220> FEATURE:
<223> OTHER INFORMATION: Lactobacillus_plantarum_ATG-K2_16S_rRNA_
      sequence_partial

<400> SEQUENCE: 1
taggcggctg gttcctaaaa ggttacccca ccgactttgg gtgttacaaa ctctcatggt      60
gtgacgggcg gtgtgtacaa ggcccgggaa cgtattcacc gcggcatgct gatccgcgat     120
tactagcgat tccgacttca tgtaggcgag ttgcagccta caatccgaac tgagaatggc     180
tttaagagat tagcttactc tcgcgagttc gcaactcgtt gtaccatcca ttgtagcacg     240
tgtgtagccc aggtcataag gggcatgatg atttgacgtc atccccacct tcctccggtt     300
tgtcaccggc agtctcacca gagtgcccaa cttaatgctg gcaactgata ataagggttg     360
cgctcgttgc gggacttaac ccaacatctc acgacacgag ctgacgacaa ccatgcacca     420
cctgtatcca tgtccccgaa gggaacgtct aatctcttag atttgcatag tatgtcaaga     480
cctggtaagg ttcttcgcgt agcttcgaat taaaccacat gctccaccgc ttgtgcgggc     540
ccccgtcaat tcctttgagt ttcagccttg cggccgtact ccccaggcgg aatgcttaat     600
gcgttagctg cagcactgaa gggcggaaac cctccaacac ttagcattca tcgtttacgg     660
tatggactac cagggtatct aatcctgttt gctacccata ctttcgagcc tcagcgtcag     720
ttacagacca gacagccgcc ttcgccactg gtgttcttcc atatatctac gcatttcacc     780
gctacacatg gagttccact gtcctcttct gcactcaagt ttcccagttt ccgatgcact     840
tcttcggttg agccgaaggc tttcacatca gacttaaaaa accgcctgcg ctcgctttac     900
gcccaataaa tccggacaac gcttgccacc tacgtattac cgcggctgct ggcacgtagt     960
```

```
tagccgtggc tttctggtta aataccgtca atacctgaac agttactctc agatatgttc    1020
ttctttaaca acagagtttt acgagccgaa acccttcttc actcacgcgg cgttgctcca    1080
tcagactttc gtccattgtg gaagattccc tactgctgcc tcccgtagga gtttgggccg    1140
tgtctcagtc ccaatgtggc cgattaccct ctcaggtcgg ctacgtatca ttgccatggt    1200
gagccgttac ctcaccatct agctaatacg ccgcgggacc atccaaaagt gatagccgaa    1260
gccatctttc aaactcggac catgcggtcc aagttgttat gcggtattag catctgtttc    1320
caggtgttat cccccgcttc tgggcaggtt tcccacgtgt tactcaccag ttcgccactc    1380
actcaaatgt aaatcatgat gcaagcacca atcaatacca gagttcgttc gacttgcatg    1440
tattaggcac gccgccagcg ttcgtcctga gccatgtcca aa                       1482
```

```
<210> SEQ ID NO 2
<211> LENGTH: 1474
<212> TYPE: DNA
<213> ORGANISM: Unknown
<220> FEATURE:
<223> OTHER INFORMATION: Lactobacillus_plantarum_ATG-K6_16S_rRNA_
      sequence_partial

<400> SEQUENCE: 2
cttaggcggc tggttcctaa aaggttaccc caccgacttt gggtgttaca aactctcatg     60
gtgtgacggg cggtgtgtac aaggcccggg aacgtattca ccgcggcatg ctgatccgcg    120
attactagcg attccgactt catgtaggcg agttgcagcc tacaatccga actgagaatg    180
gctttaagag attagcttac tctcgcgagt tcgcaactcg ttgtaccatc cattgtagca    240
cgtgtgtagc ccaggtcata aggggcatga tgatttgacg tcatccccac cttcctccgg    300
tttgtcaccg gcagtctcac cagagtgccc aacttaatgc tggcaactga taataagggt    360
tgcgctcgtt gcgggactta acccaacatc tcacgacacg agctgacgac aaccatgcac    420
cacctgtatc catgtccccg aagggaacgt ctaatctctt agatttgcat agtatgtcaa    480
gacctggtaa ggttcttcgc gtagcttcga attaaaccac atgctccacc gcttgtgcgg    540 gccccccgtca attcctttga gtttcagcct tgcggccgta ctcccaggc ggaatgctta    600 atgcgttagc tgcagcactg aagggcggaa accctccaac acttagcatt catcgtttac    660
ggtatggact accagggtat ctaatcctgt ttgctaccca tactttcgag cctcagcgtc    720
agttacagac cagacagccg ccttcgccac tggtgttctt ccatatatct acgcatttca    780
ccgctacaca tggagttcca ctgtcctctt ctgcactcaa gtttcccagt ttccgatgca    840
cttcttcggt tgagccgaag ctttcacat cagacttaaa aaaccgcctg cgctcgcttt    900
acgcccaata atccggaca acgcttgcca ctacgtatt accgcggctg ctggcacgta    960
gttagccgtg gctttctggt taaataccgt caatacctga acagttactc tcagatatgt    1020
tcttctttaa caacagagtt ttacgagccg aaaccttct tcactcacgc ggcgttgctc    1080
catcagactt tcgtccattg tggaagattc cctactgctg cctcccgtag gagtttggg    1140 cgtgtctcag tcccaatgtg gccgattacc ctctcaggtc ggctacgtat cattgccatg    1200
gtgagccgtt accccaccat ctagctaata cgccgcggga ccatccaaaa gtgatagccg    1260
aagccatctt tcaagctcgg accatgcggt ccaagttgtt atgcggtatt agcatctgtt    1320
tccaggtgtt atccccgct tctgggcagg tttcccacgt gttactcacc agttcgccac    1380
tcactcaaat gtaaatcatg atgcaagcac caatcaatac cagagttcgt tcgacttgca    1440
tgtattaggc acgccgccag cgttcgtcct gagc                                1474
```

<210> SEQ ID NO 3
<211> LENGTH: 1476
<212> TYPE: DNA
<213> ORGANISM: Unknown
<220> FEATURE:
<223> OTHER INFORMATION: Lactobacillus_plantarum_ATG-K8_16S_rRNA_
      sequence_partial

<400> SEQUENCE: 3
cttaggcggc tggttcctaa aaggttaccc caccgacttt gggtgttaca aactctcatg      60
gtgtgacggg cggtgtgtac aaggcccggg aacgtattca ccgcggcatg ctgatccgcg     120
attactagcg attccgactt catgtaggcg agttgcagcc tacaatccga actgagaatg     180
gctttaagag attagcttac tctcgcgagt tcgcaactcg ttgtaccatc cattgtagca     240
cgtgtgtagc ccaggtcata agggcatga tgatttgacg tcatccccac cttcctccgg     300
tttgtcaccg gcagtctcac cagagtgccc aacttaatgc tggcaactga taataagggt     360
tgcgctcgtt gcgggactta acccaacatc tcacgacacg agctgacgac aaccatgcac     420
cacctgtatc catgtccccg aagggaacgt ctaatctctt agatttgcat agtatgtcaa     480
gacctggtaa ggttcttcgc gtagcttcga attaaaccac atgctccacc gcttgtgcgg     540 gccccgtca attcctttga gtttcagcct tgcggccgta ctccccaggc ggaatgctta     600
atgcgttagc tgcagcactg aagggcggaa accctccaac acttagcatt catcgtttac     660
ggtatggact accagggtat ctaatcctgt ttgctaccca tactttcgag cctcagcgtc     720
agttacagac cagacagccg ccttcgccac tggtgttctt ccatatatct acgcatttca     780
ccgctacaca tggagttcca ctgtcctctt ctgcactcaa gtttcccagt ttccgatgca     840
cttcttcggt tgagccgaag gctttcacat cagacttaaa aaaccgcctg cgctcgcttt     900
acgcccaata aatccggaca acgcttgcca cctacgtatt accgcggctg ctggcacgta     960
gttagccgtg gctttctggt taaataccgt caataccga acagttactc tcagatatgt    1020
tcttctttaa caacagagtt ttacgagccg aaacccttct tcactcacgc ggcgttgctc    1080
catcagactt tcgtccattg tggaagattc cctactgctg cctcccgtag gagtttgggc    1140
cgtgtctcag tcccaatgtg gccgattacc ctctcaggtc ggctacgtat cattgccatg    1200
gtgagccgtt accccaccat ctagctaata cgccgcggga ccatccaaaa gtgatagccg    1260
aagccatctt tcaaactcgg accatgcggt ccaagttgtt atgcggtatt agcatctgtt    1320
tccaggtgtt atccccgct tctgggcagg tttcccacgt gttactcacc agttcgccac    1380
tcactcaaat gtaaatcatg atgcaagcac caatcaatac cagagttcgt tcgacttgca    1440
tgtattaggc acgccgccag cgttcgtcct gagcca                             1476

<210> SEQ ID NO 4
<211> LENGTH: 20
<212> TYPE: DNA
<213> ORGANISM: Unknown
<220> FEATURE:
<223> OTHER INFORMATION: 27F

<400> SEQUENCE: 4
agagtttgat cctggctcag                                                 20

<210> SEQ ID NO 5
<211> LENGTH: 19
<212> TYPE: DNA
<213> ORGANISM: Unknown
<220> FEATURE:

```
<223> OTHER INFORMATION: 518F

<400> SEQUENCE: 5
ccagcagccg cggtaatac                                                   19

<210> SEQ ID NO 6
<211> LENGTH: 20
<212> TYPE: DNA
<213> ORGANISM: Unknown
<220> FEATURE:
<223> OTHER INFORMATION: 907R

<400> SEQUENCE: 6
ccgtcaattc mtttragttt                                                  20

<210> SEQ ID NO 7
<211> LENGTH: 19
<212> TYPE: DNA
<213> ORGANISM: Unknown
<220> FEATURE:
<223> OTHER INFORMATION: 1492R

<400> SEQUENCE: 7
ggttaccttg ttacgactt                                                   19
```

LACTOBACILLUS PLANTARUM STRAIN ATG-K2, ATG-K6 OR ATG-K8, AND COMPOSITION FOR PREVENTING OR TREATING VAGINITIS COMPRISING SAME

CROSS REFERENCE TO RELATED APPLICATIONS

This application is a National Stage of International Application No. PCT/KR2019/006936 filed Jun. 10, 2019, claiming priority based on Korean Patent Application No. 10-2018-0121634 filed Oct. 12, 2018, the entire disclosures of which are incorporated herein by reference.

TECHNICAL FIELD

The present disclosure relates to a novel *Lactobacillus plantarum* strain ATG-K2, ATG-K6 or ATG-K8 and a composition for preventing or treating vaginitis containing the same.

BACKGROUND ART

Vaginitis is an inflammatory disease occurring in the female urogenital system, and vaginitis may be broadly classified into infectious and non-infectious forms, and it is not easy to self-diagnose the cause of the onset before accurate medical analysis. Typical symptoms of vaginitis include odor, excessive secretion, increased pH, inflammatory swelling, erythema, skin cracking and the like (Morris et al., 2001; Egan and Lipsky, 2002). Among these, the breakdown of infectious vaginitis is expected to be 40-50% of bacterial vaginosis, 25-25% of vaginal candidiasis, and 15-20% of trichomonal vaginitis (Sobel, 1997; Egan and Lipsky, 2002). In general, treatment is attempted with antibiotics, antifungal agents or combined oral administration or direct administration to the affected area, depending on the cause of the infection. In infectious vaginitis, *Gardnerella vaginalis* is the main microorganism causing bacterial vaginosis, and *Candida albicans* is the main microorganism causing vaginal candidiasis. The critical pathogenesis of these infectious diseases is that the amount of lactobacilli capable of producing hydrogen peroxide is decreased in the vagina due to various causes such as excessive antibiotics, stress, primary vaginitis caused by internal factors, and the like, and eventually, direct disinfection by hydrogen peroxide and production of lactic acid from lactobacilli are significantly reduced, thus increasing the pH, creating an environment in which various bacteria easily grow (Sobel, 1997). Hence, lactic-acid bacteria capable of lowering the pH again are added, and in particular, supplementation with lactic-acid bacteria having the ability to produce hydrogen peroxide is regarded as an important method in the improvement in female genital health.

Therefore, the inventors of the present disclosure have performed various studies on methods of reducing vaginitis using lactic-acid bacteria, and have ascertained that a novel *Lactobacillus plantarum* strain ATG-K2, ATG-K6 or ATG-K8 has antimicrobial effects against a variety of vaginitis pathogens and has superior immunity-enhancing efficacy, thus culminating in the present disclosure.

CITATION LIST

Patent Literature (Patent Document 1) Korean Patent No. 10-1750468 (Title: Composition comprising *Lactobacillus fermentum* MG901 or *Lactobacillus plantarum* MG989, Applicant: Mediogen Co. Ltd., et al., Registration date: Jun. 19, 2017)

(Patent Document 2) Korean Patent No. 10-1098241 (Title: *Lactobacillus* sp. HY7801 having inhibitory effect against urinary tract infection and candidiasis, and products containing the same as effective component, Applicant: Korea Yakult Co. Ltd., Registration date: Dec. 19, 2011)

(Patent Document 3) Korean Patent No. 10-1860513 (Title: Pharmaceutical composition for preventing or treating candidal colpitis comprising *Lactobacillus salivarius* MG242 isolated from human vagina, Applicant: Mediogen Co. Ltd., et al., Registration date: May 16, 2018)

(Patent Document 4) Korean Patent No. 10-1784847 (Title: A composition comprising lactic-acid bacteria for protecting and treating vaginosis disease and the use thereof, Applicant: Haudongchun Co. Ltd., Registration date: Sep. 28, 2017)

Non-Patent Literature (Non-Patent Document 1) Aslim B., Onal D., Beyatli Y. 2007. Factors influencing autoaggregation and aggregation of *Lactobacillus delbrueckii* subsp. *bulgaricus* isolated from handmade yogurt. J. Food Protec. 70:223-227.

(Non-Patent Document 2) Begley M., Hill C., Gahan CGM. 2006. Bile salt hydrolase activity in probiotics. Appl Environ Microbiol 72:1729-1738.

(Non-Patent Document 3) Bover-Cid S., Holzapfel W. H. 1999. Improved screening procedure for biogenic amine production by lactic-acid bacteria. Int. J. Food Microbiol. 53:33-41.

(Non-Patent Document 4) Dashkevicz M. P., Feighner S. D. 1989. Development of a differential medium for bile salt hydrolase-active *Lactobacillus* spp. Appl. Envrion. Microbiol. 55:11-16.

(Non-Patent Document 5) de Vries M. C., Vaughan E. E., Kleerebezem M., de Vos W. M. 2006. *Lactobacillus plantarum*—survival, functional and potential probiotic properties in the human intestinal tract. Int. Dairy J. 16: 1018-1028.

(Non-Patent Document 6) EFSA Panel on Additives and Products or Substances used in Animal Feed (FEEDAP). 2012. Guidance on the assessment of bacterial susceptibility to antimicrobials of human and veterinary importance. EFSA Journal 10(6):2740.

(Non-Patent Document 7) Egan M., Lipsky M. S. 2002. Vaginitis: case reports and brief review. AIDS Patient Care STDS 16:367-373.

(Non-Patent Document 8) Fielding C. A., MacLoughlin R. M., McLeod L., Colmont C. S., Najdovska M., Grail D., et al. 2008. IL-6 regulates neutrophil trafficking during acute inflammation via STAT3. J. Immunol. 181:2189-2195.

(Non-Patent Document 9) Fiorentino D. F., Zlotnik A., Mosmann T. R., Howard M., O'Garra. 1991. IL-10 inhibits cytokine production by activated macrophages. J. Immunol. 147:3815-3822.

(Non-Patent Document 10) Handley P. S., Harty D. W. S., Wyatt J. W., Brown C. R., Doran J. P., Gibbs A. C. 1987. A comparison of the adhesion, coaggregation and cell-surface hydrophobicity properties of fibrillary and fimbriate strains of *Streptococcus salivarius*. J. Gen. Microbiol. 133:3207-3217.

(Non-Patent Document 11) McGroarty J. A., Tomeczek L., Pond D. G., Reid G., Bruce A. W. 1992. Hydrogen peroxide production by *Lactobacillus* species: correlation with susceptibility to the spermicidal compound nonoxynol-9. J. Infect. Diseases 165:1142-1144.
(Non-Patent Document 12) Morris M., Nicoll A., Simms I., Wilson J., Catchpole M. 2001. Bacterial vaginosis: a public health review. Br. J. Obstet. Gynaecol. 108:439-450.
(Non-Patent Document 13) Scheller J., Chalaris A., Schmidt-Arras D., Rose-John S. 2001. The pro- and anti-inflammatory properties of the cytokine interleukin-6. Biochim. Biophys. Acta 1813(5):878-888.
(Non-Patent Document 14) Sobel J. D. 1997. Vaginitis. N. Engl. J. Med. 337:1896-1903.
(Non-Patent Document 15) Vujanovic N. L. 2011. Role of TNF superfamily ligands in innate immunity. Immunol. Res. 50:159-174.

DISCLOSURE

Technical Problem

An objective of the present disclosure is to provide a novel *Lactobacillus plantarum* strain ATG-K2, ATG-K6 or ATG-K8, and a composition for the prevention or treatment of vaginitis containing the same.

Technical Solution

The present disclosure pertains to *Lactobacillus plantarum* ATG-K2 (Accession number: KCTC 13577BP), *Lactobacillus plantarum* ATG-K6 (Accession number: KCTC 13570BP) or *Lactobacillus plantarum* ATG-K8 (Accession number: KCTC 13571BP), all of which have antimicrobial activity against at least one vaginitis pathogen selected from *Candida albicans* and *Gardnerella vaginalis*.

The *Lactobacillus plantarum* ATG-K2, *Lactobacillus plantarum* ATG-K6 or *Lactobacillus plantarum* ATG-K8 has antimicrobial activity against at least one bacterium selected from the group consisting of *Staphylococcus aureus, Listeria monocytogenes, Streptococcus mutans, Streptococcus salivarius, Escherichia coli, Pseudomonas aeruginosa,* and *Cronobacter sakazakii*.

The *Lactobacillus plantarum* ATG-K2, *Lactobacillus plantarum* ATG-K6 or *Lactobacillus plantarum* ATG-K8 does not cause hemolysis and does not produce at least one biogenic amine selected from the group consisting of histamine, tyramine, putrescine, and cadaverine.

The *Lactobacillus plantarum* ATG-K2, *Lactobacillus plantarum* ATG-K6 or *Lactobacillus plantarum* ATG-K8 has bile salt hydrolase activity, and also has the ability to produce hydrogen peroxide or antioxidant activity.

The *Lactobacillus plantarum* ATG-K2, *Lactobacillus plantarum* ATG-K6 or *Lactobacillus plantarum* ATG-K8 is not resistant to at least one antibiotic selected from the group consisting of ampicillin, vancomycin, gentamicin, kanamycin, streptomycin, clindamycin, erythromycin, tetracycline, and chloramphenicol.

The *Lactobacillus plantarum* ATG-K2, *Lactobacillus plantarum* ATG-K6 or *Lactobacillus plantarum* ATG-K8 has innate immune activity that increases the amount of at least one cytokine selected from among IL-6 (interleukin-6) and TNF-$\alpha$ (tumor necrosis factor-$\alpha$), and has anti-inflammatory activity that increases the amount of IL-10 (interleukin-10).

The present disclosure pertains to a pharmaceutical composition for the treatment or amelioration of vaginitis containing the *Lactobacillus plantarum* ATG-K2, *Lactobacillus plantarum* ATG-K6 or *Lactobacillus plantarum* ATG-K8.

The present disclosure provides a functional health food for the prevention or amelioration of vaginitis containing the *Lactobacillus plantarum* ATG-K2, *Lactobacillus plantarum* ATG-K6 or *Lactobacillus plantarum* ATG-K8.

The strain of the present disclosure may be cultured in an MRS liquid or solid medium (broth or agar), and in the MRS broth, *Lactobacillus plantarum* K2 may be cultured to a concentration of about $5\times10^8$ CFU/ml, *Lactobacillus plantarum* K6 may be cultured to a concentration of about $3\times10^9$ CFU/ml, and *Lactobacillus plantarum* K8 may be cultured to a concentration of about $3\times10^9$ CFU/ml.

These strains are preferably cultured at 30 to 37° C. for 16 to 48 hr, and the optimal culture temperature is 37° C., the minimum culture temperature is 15° C., the maximum culture temperature is 38° C., the optimal culture pH is 6.5, the minimum culture pH is 4.0, and the maximum culture pH is 7.8. The optimal culture time is 16 hr, the minimum culture time is 10 hr, and the maximum culture time is 120 hr.

In addition, the present disclosure provides a pharmaceutical composition for the prevention or treatment of vaginitis containing the novel *Lactobacillus plantarum* strain ATG-K2, ATG-K6 or ATG-K8. The novel *Lactobacillus plantarum* strain ATG-K2, ATG-K6 or ATG-K8 may be added in an amount of 0.001 to 30 wt % to the pharmaceutical composition of the present disclosure.

The pharmaceutical composition may be formulated into oral dosage forms, such as powders, granules, tablets, capsules, suspensions, emulsions, syrups, and aerosol formulations, as well as formulations for external use, suppositories, and the like, in accordance with typical individual processes. A carrier, an excipient and a diluent, which may be contained in the pharmaceutical composition, may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. The formulation may be typically prepared using a diluent or excipient such as a filler, an extender, a binder, a wetting agent, a disintegrant, a surfactant, and the like. A solid formulation for oral administration may include tablets, pills, powders, granules, capsules, and the like, and such a solid formulation may be prepared by mixing the strain of the present disclosure with at least one excipient, for example, starch, calcium carbonate, sucrose, lactose, gelatin, and the like. In addition to a simple excipient, lubricants such as magnesium stearate, talc and the like may be used. An oral liquid formulation may include suspensions, solutions, emulsions, syrups, and the like, and may also include not only simple diluents, such as water or liquid paraffin, but also various excipients, for example, wetting agents, sweeteners, fragrances, preservatives, and the like. A formulation for parenteral administration may include sterilized aqueous solutions, non-aqueous solvents, suspensions, emulsions, lyophilized preparations, suppositories, and vaginal suppositories. As non-aqueous solvents or suspension agents, propylene glycol, polyethylene glycol, vegetable oil such as olive oil, injectable esters such as ethyl oleate and the like may be used. As the base of a suppository, Witepsol, Macrogol, Tween 61, cacao butter, laurin fat, glycerogelatin and the like may be used.

The amount of the pharmaceutical composition according to the present disclosure, when administered, may vary depending on the age, gender and weight of the subject to be treated, the particular disease or pathological condition for treatment, the severity of the disease or pathological condition, the administration route, and the judgment of the prescriber. A dose determination based on these factors will be easily made by those skilled in the art, and the dose typically falls in the range of 0.01 mg/kg/day to about 2000 mg/kg/day. Preferably, the dose is set to the range of 1 mg/kg/day to 500 mg/kg/day. The administration may be carried out once a day or several times a day. The dose does not in any way limit the scope of the present disclosure.

The pharmaceutical composition according to the present disclosure may be administered to mammals such as mice, livestock, humans, and the like through various routes. Since the strain of the present disclosure has little toxicity and minimal side effects, it is a drug that may be safely used even when taken for a long time for prophylactic purposes.

In addition, the present disclosure provides a functional health food for the prevention or amelioration of vaginitis containing the novel *Lactobacillus plantarum* strain ATG-K2, ATG-K6 or ATG-K8. The *Lactobacillus plantarum* strain ATG-K2, ATG-K6 or ATG-K8 may be added in an amount of 0.001 to 50 wt % to the functional health food of the present disclosure. The functional health food of the present disclosure is provided in forms such as tablets, capsules, pills or liquids, and examples of the food to which the strain of the present disclosure may be added include various drinks, meats, sausages, breads, candies, snacks, noodles, ice creams, dairy products, soups, electrolytic beverages, drinking water, alcoholic beverages, gums, teas, and vitamin complexes.

Advantageous Effects

The present disclosure pertains to a novel *Lactobacillus plantarum* strain ATG-K2, ATG-K6 or ATG-K8, and a composition for the prevention or treatment of vaginitis containing the same, and the *Lactobacillus plantarum* strain ATG-K2, ATG-K6 or ATG-K8 has excellent antimicrobial effects against various pathogenic strains as well as *Candida albicans* and *Gardnerella vaginalis*, which are vaginitis pathogens, and thus can be easily used as a composition for the treatment of bacterial vaginosis, vaginal candidiasis, etc., or as a functional health food for the prevention or amelioration of these diseases.

BRIEF DESCRIPTION OF DRAWINGS

FIG. 1 shows the results of comparison of 16S rRNA sequences of each of the *Lactobacillus plantarum* K2 (1079-1378 of SEQ ID NO: 1), K6 (1081-1380 of SEQ ID NO: 2) and K8 (1081-1380 of SEQ ID NO: 3) strains of the present disclosure;

FIG. 2 shows the results of confirmation of heat resistance of each of the *Lactobacillus plantarum* K2, K6 and K8 strains of the present disclosure;

FIGS. 3A and 3B show the results of confirmation of hemolysis of each of the *Lactobacillus plantarum* K2, K6 and K8 strains of the present disclosure (FIG. 3) and the results of production of biogenic amine thereby (FIG. 3B);

FIGS. 4A, 4B and 4C show the results of confirmation of bile salt hydrolase activity (FIG. 4A), ability to produce hydrogen peroxide (FIG. 4B) and antioxidant activity (FIG. 4C) of each of the *Lactobacillus plantarum* K2, K6 and K8 strains of the present disclosure;

FIGS. 5A, 5B, 5C and 5D show the results of confirmation of the activity of each of the *Lactobacillus plantarum* K2, K6 and K8 strains of the present disclosure on inhibiting the growth of *Candida albicans* KCTC7678 (CA) (FIG. 5A), the activity thereof on inhibiting the growth of *Gardnerella vaginalis* KCTC5096 (GV) (FIG. 5B), the coaggregation thereof on *Candida albicans* KCTC7678 (CA) (FIG. 5C), and the coaggregation thereof on *Gardnerella vaginalis* KCTC5096 (GV) (FIG. 5D);

FIGS. 6A, 6B, 6C and 6D show the results of coculture of each of the *Lactobacillus plantarum* K2, K6 and K8 strains of the present disclosure with *Candida albicans* KCTC7678 (CA) (FIG. 6A and FIG. 6B) and the results of coculture thereof with *Gardnerella vaginalis* KCTC5096 (GV) (FIG. 6C and FIG. 6D);

FIGS. 7A and 7B show the effect of enhancing innate immunity (increased IL-6 and TNF-α levels) by each of the *Lactobacillus plantarum* K2, K6 and K8 strains of the present disclosure; and FIG. 8 shows the effect of inhibiting inflammation (increased IL-10 level) by each of the *Lactobacillus plantarum* K2, K6 and K8 strains of the present disclosure.

MODE FOR DISCLOSURE

A better understanding of the present disclosure will be obtained through the following examples. However, the present disclosure is not limited to these examples, and may be embodied in other forms. These examples are provided to thoroughly explain the disclosure and to sufficiently transfer the spirit of the present disclosure to those skilled in the art.

Example 1. Preparation of Lactic-Acid Bacteria and Infectious Microorganisms

The lactic-acid bacteria that were used were *Lactobacillus plantarum* ATG-K2 (K2), *Lactobacillus plantarum* ATG-K6 (K6), and *Lactobacillus plantarum* ATG-K8 (K8), which are new microorganisms isolated from kimchi samples in the Chungcheong region, Korea in January 2016. The bacteria used in the antimicrobial test were seven types of infectious or opportunistic bacteria, including *Staphylococcus aureus* KCTC1621 (SA), *Escherichia coli* KCTC1682 (EC), *Pseudomonas aeruginosa* KCTC2004 (PA), *Listeria monocytogenes* KCTC3569 (LM), *Cronobacter sakazakii* KCTC2949 (CS), *Streptococcus mutans* KCTC3065 (SM), and *Streptococcus salivarius* ATG-P1 (SS). As for vaginitis pathogens, *Candida albicans* KCTC7678 (CA) was used as a fungal model, and *Gardnerella vaginalis* KCTC5096 (GV) was used as a bacterial model. Lactic-acid bacteria were cultured in an MRS (Difco Laboratories, USA) agar or broth medium, and bacteria other than GV were cultured in a BHI (Brain Heart Infusion, Difco Laboratories, USA) agar or broth medium. GV was inoculated into a BHI agar or broth medium containing 20% of heat-treated horse serum (Gibco, USA), followed by anaerobic culture using an Oxoid™ AnaeroGen™ system (Oxoid, UK). CA was cultured in a YM (Difco Laboratories, USA) agar or broth medium. All microorganisms were subjected to stationary culture at 37° C. for about 20 hr.

Example 2. Confirmation of Physiological Properties of Lactic-Acid Bacteria

Example 2-1. Identification of 16S rRNA Sequence of Lactic-Acid Bacteria

For molecular biological identification, the 16S rRNA sequencing of lactic-acid bacteria K2, K6 and K8 strains isolated from kimchi was performed by Solgent (Daejeon). Using 27F (5'-AGA GTT TGA TCC TGG CTC AG-3'; SEQ ID NO: 4), 518F (5'-CCA GCA GCC GCG GTA ATA C-3';

SEQ ID NO: 5), 907R (5'-CCG TCA ATT CMT TTR AGT TT-3'; SEQ ID NO: 6), and 1492R (5'-GGT TAC CTT GTT ACG ACT T-3'; SEQ ID NO: 7) as primers for sequencing, nucleotide sequence reading was performed a total of four times, and the contigs obtained through nucleotide sequence alignment of each reading were analyzed using a BLAST online tool (hypertext transfer protocol: blast.ncbi.nlm.nih.gov/Blast.cgi) of the National Center for Biotechnology Information (NCBI). Using Clustal Omega (hypertext transfer protocol: www.ebi.ac.uk/Tools/msa/clustalo) of EMBL-EBI, the differences in 16S rRNA sequences between the K2, K6 and K8 strains were analyzed.

Based on the results of 16S rRNA sequencing, respective strains are confirmed to have the nucleotide sequences of SEQ ID NOS: 1 to 3 below, and as shown in FIG. 1, the nucleotide sequences of three types of strains were identical to *Lactobacillus plantarum*, and when the nucleotide sequences of K2, K6 and K8 strains were compared, it appeared that one nucleotide was different between the nucleotide sequences (FIG. 1).

```
SEQ ID NO: 1: Lactobacillus_plantarum_ATG-
K2_16S_rRNA_sequence_partial
TAGGCGGCTGGTTCCTAAAAGGTTACCCCACCGACTTTGGGTGTTACAAA

CTCTCATGGTGTGACGGGCGGTGTGTACAAGGCCCGGGAACGTATTCACC

GCGGCATGCTGATCCGCGATTACTAGCGATTCCGACTTCATGTAGGCGAG

TTGCAGCCTACAATCCGAACTGAGAATGGCTTTAAGAGATTAGCTTACTC

TCGCGAGTTCGCAACTCGTTGTACCATCCATTGTAGCACGTGTGTAGCCC

AGGTCATAAGGGGCATGATGATTTGACGTCATCCCCACCTTCCTCCGGTT

TGTCACCGGCAGTCTCACCAGAGTGCCCAACTTAATGCTGGCAACTGATA

ATAAGGGTTGCGCTCGTTGCGGGACTTAACCCAACATCTCACGACACGAG

CTGACGACAACCATGCACCACCTGTATCCATGTCCCCGAAGGGAACGTGT

AATCTCTTAGATTTGCATAGTATGTCAAGACCTGGTAAGGTTCTTCGCGT

AGCTTCGAATTAAACCACATGCTCCACCGCTTGTGCGGGCCCCCGTCAAT

TCCTTTGAGTTTCAGCCTTGCGGCCGTACTCCCCAGGCGGAATGCTTAAT

GCGTTAGCTGCAGCACTGAAGGGCGGAAACCCTCCAACACTTAGCATCAT

CGTTTACGGTATGGACTACCAGGGTATCTAATCCTGTTTGCTACCCATAC

TTTCGAGCCTCAGCGTCAGTTACAGACCAGACAGCCGCCTTCGCCACTGG

TGTTCTTCCATATATCTACGCATTTCACCGCTACACATGGAGTTCCACTG

TCCTCTTCTGCACTCAAGTTTCCCAGTTTCCGATGCACTTCTTCGGTTGA

GCCGAAGGCTTTCACATCAGACTTAAAAAACCGCCTGCGCTCGCTTTACG

CCCAATAAATCCGGACAACGCTTGCCACCTACGTATTACCGCGGCTGCTG

GCACGTAGTTAGCCGTGGCTTTCTGGTTAAATACCGTCAATACCTGAACA

GTTACTCTCAGATATGTTCTTCTTTAACAACAGAGTTTTACGAGCCGAAA

CCCTTCTTCACTCACGCGGCGTTGCTCCATCAGACTTTCGTCCATTGTGG

AAGATTCCCTACTGCTGCCTCCCGTAGGAGTTTGGGCCGTGTCTCAGTCC

CAATGTGGCCGATTACCCTCTCAGGTCGGCTACGTATCATTGCCATGGTG

AGCCGTTACCTGACCATCTAGCTAATACGCCGCGGGACCATCCAAAAGTG

ATAGCCGAAGCCATCTTTCAAACTCGGACCATGCGGTCCAAGTTGTTATG

CGGTATTAGCATCTGTTTCCAGGTGTTATCCCCCGCTTCTGGGCAGGTTT

CCCACGTGTTACTCACCAGTTCGCCACTCACTCAAATGTAAATCATGATG

CAAGCACCAATCAATACCACACTTCGTTCGACTTGCATGTATTAGGCACG

CCGCCAGCGTTCGTCCTGAGCCATGTCCAAA

SEQ ID NO: 2: Lactobacillus_plantarum_ATG-
K2_16S_rRNA_sequence_partial
CTTAGGCGGCTGGTTCCTAAAAGGTTACCCCACCGACTTTGGGTGTTACA

AACTCTCATGGTGTGACGGGCGGTGTGTACAAGGCCCGGGAACGTATTCA

CCGCGGCATCCTGATCCGCGATTACTAGCGATTCCGACTTCATGTAGGCG

AGTTGCAGCCTACAATCCGAACTGAGAATGGCTTTAAGAGATTAGCTTAC

TCTCGCGAGTTCGCAACTCGTTGTACCATCCATTGTAGCACGGTGTAGCC

CAGGTCATAAGGGGCATGATGATTTGACGTCATCCCCACCTTCCTCCGGT

TTGTCACCGGCAGTCTCACCAGAGTGCCCAACTTAATGCTGGCAACTGAT

AATAAGGGTTGCGCGTCGTTGCGGGACTTAACCCAACATCTCACGACACG

AGCTGACGACAACCATGCACCACCTGTATCCATGTCCCCGAAGGGAACGT

CTAATCTCTTAGATTTGCATAGTATGTCAAGACCTGGTAAGGTTCTTCGC

GTAGCTTCGAATTAAACCACATGCTCCACCGCTTGTGCGGGCCCCCGTCA

ATTCCTTTGATTTTCAGCCTTGCGGCCGTACTCCCCAGGCGGAATGCTTA

ATGCGTTAGCTGCAGCACTGAAGGGCGGAAACCCTCCAACACTTAGCATT

CATCGTTTACGGTATGGACTACCAGGGTATCTAATCCTGTTTGCTACCCA

TACTTTCGAGCCTCAGCGTCAGTTACAGACCAGACAGCCGCCTTCGCCAC

TGGTGTTCTTCCATATATCTACGCATTTCACCGCTACACATGGAGTTCCA

CTGTCCTCTTCTGCACTCAAGTTTCCCAGTTTCCGATGCACTTCTTCGGT

TGAGCCGAAGGCTTTCACATCAGACTTAAAAAACCGCCTGCGCTCGCTTT

ACGCCCAATAAATCCGGACAACGCTTGCCACCTACGTATTACCGCGGCTG

CTGGCACGTAGTTAGCCGTGGCTTTTGGTTAAATACCGTCAATACCTGAA

CAGTTACTCTCAGATATGTTCTTCTTAACAACAGAGTTTTACGAGCCGAA

ACCCTTCTTCACTCACGCGGCGTTGCTCCATCAGACTTTCGTCCATTGTG

GAAGATTCCCTACTGCTGCCTCCCGTAGGAGTTGGGCCGTGTCTCAGTCC

CAATGTGGCCGATTACCCTCTCAGGTCGGCTACGTATCATTGCCATGGTG

AGCCGTTACCCCACCATCTAGCTAATACGCCGCGGGACCATCCAAAAGTG

ATAGCCGAAGCCATCTTTCAAGCTCGGACCATGCGGTCCAAGTTGTTATG

CGGTATTAGCATCTGTTTCCAGGTGTTATCCCCCGCTTCTGGGCAGGTTT

CCCACGTGTTACTCACCAGTTCGCCACTCACTCAAATGTAAATCATGATG

CAAGCACCAATCAATACCAGAGTTCGTTCGACTTGCATGTATTAGGCACG

CCGCCAGCGTTCGTCCTGAGC

SEQ ID NO: 3: Lactobacillus_plantarum_ATG-
K8_16S_rRNA_sequence_partial
CTTAGGCGGCTGGTTCCTAAAAGGTTACCCCACCGACTTTGGGTGTGGAC

AAACTCTCATGGTGTGACGGGCGGTGTGTACAAGGCCCGGGAACGTATTC

ACCGCGGCATGCTGATCCGCGATTACTAGCGATTCCGACTTCATGTAGGC

GAGTTGCAGCCTACAATCCGAACTGAGAATGGCTTTAAGAGATTAGCTTA

CTCTCGCGAGTTCGCAACTCGTTGTACCATCCATTGTAGCACGTGTGTAG
```

```
-continued
CCCAGGTCATAAGGGGCATGATGATTTGACGTCATCCCCACCTTCCTCCG

GTTTGTCACCGGCAGTCTCACCAGAGTGCCCAACTTAATGCTGGCAACTG

ATAATAAGGGTTGCGCTCGTTGCGGGACTTAACCCAACATCTCACGACAC

GAGCTGACGACAACCATGCACCACCTGTATCCATGTCCCCGAAGGGAACG

TCTAATCTCTTAGATTTGCATAGTATGTCAAGACCTGGTAAGGTTCTTCG

CGTAGCTTCGAATTAAACCACATGCTCCACCGCTTGTGCGGGCCCCCGTC

AATTCCTTTGAGTTTCAGCCTTGCGGCCGTACTCCCCAGGCGGAATGCTT

AATGCGTTAGCTGCAGCACTGAAGGGCGGAAACCCTCCAACACTTAGCTT

CATCGTTTACGGTATGGACTACCAGGGTATCTAATCCTGTTTGCTACCCA

TACTTTCGAGCCTCAGCGTCAGTTACAGACCAGACAGCCGCCTTCGCCAC

TGGTGTTCTTCCATATATCTACGCATTTCACCGCTACACATGGAGTTCCA

CTGTCCTCTTCTGCACTCAAGTTTCCCAGTTTCCGATGCACTTCTTCGGT

TGAGCCGAAGGCTTTCACATCGAGACTTAAAAAACCGCCTGCGCTCGCTTT

ACGCCCAATAAATCCGGACAACGCTTGCCACCTACGTATTACCGCGGCTG

CTGGCACGTAGTTAGCCGTGGCTTTCTGGTTAAATACCGTCAATACCTGA

ACAGTTACTCTCAGATATGTTCTTCTTTAACAACAGAGTTTTACGAGCCG

AAACCCTTCTTCACTCACGCGGCGTTGCTCCATCAGACTTTCGTCCATTG

TGGAAGATTCCCTACTGCGCCTCCCGTAGGAGTTTGGGCCGTGTCTCAGT

CCCAATGTGGCCGATTACCCTCTCAGGTCGGCTACGTATCATTGCCATGG

TGAGCCGTTACCCCACCATCTAGCTAATACGCCGCGGGACCATCCAAAAG

TGATAGCCGAAGCCATCTTTCAAACTCGGACCATGCGGTCCAAGTTGTTA

TGCGGTATTAGCATCTGTTTCCAGGTGTATCCCCCGCTTCTGGGCAGGTT

TCCCACGTGTTACTCACCAGTTCGCCACTCACTCAAATGTAAATCATGAT

GCAAGCACCAATCAATACCAGAGTTCGTTCGACTTGCATGTATTAGGCAC

GCCGCCAGCGTTCGTCCTGAGCCA
```

Example 2-2. Confirmation of Sugar Fermentation Pattern Characteristics

An API50 CH test (BioMerieux, France) was conducted in order to investigate identification and characteristics through a sugar fermentation pattern.

Briefly, lactic-acid bacteria that were cultured to purity in 10 ml of an API 50CHL medium (BioMerieux, France) were suspended until an absorbance $OD_{600}$ of about 0.5 was obtained, after which the culture suspension was inoculated into each cupule of an API 50CH test strip and cultured at 37° C. The results of sugar fermentation were confirmed 24, 48, and 72 hr after inoculation, and the results thereof are shown in Table 1 below.

TABLE 1

| Carbohydrates | Lb. plantarum ATG-K2 | Lb. plantarum ATG-K6 | Lb. plantarum ATG-K8 |
|---|---|---|---|
| Glycerol | − | − | − |
| Erythritol | − | − | − |
| D-Arabinose | − | − | − |
| L-Arabinose | − | w | − |
| Ribose | + | + | + |
| D-Xylose | − | − | − |

TABLE 1-continued

| Carbohydrates | Lb. plantarum ATG-K2 | Lb. plantarum ATG-K6 | Lb. plantarum ATG-K8 |
|---|---|---|---|
| L-Xylose | − | − | − |
| Adonitol | − | − | − |
| Methyl-βD-Xylopyranoside | − | − | − |
| Galactose | + | + | + |
| Glucose | + | + | + |
| Fructose | + | + | + |
| Mannose | + | + | + |
| Sorbose | − | − | − |
| Rhamnose | − | − | − |
| Dulcitol | − | − | − |
| Inositol | − | − | − |
| Mannitol | + | + | + |
| Sorbitol | + | + | + |
| Methyl-αD-Mannopyranoside | − | − | − |
| Methyl-αD-Glucopyranoside | − | − | − |
| N-Acetylglucosamine | + | + | + |
| Amygdalin | + | + | + |
| Arbutin | + | + | + |
| Esculin | + | + | + |
| Salicin | + | + | + |
| Cellobiose | + | + | + |
| Maltose | + | + | + |
| Lactose | + | + | + |
| Melibiose | + | + | + |
| Sucrose | + | + | + |
| Trehalose | + | + | + |
| Inulin | − | − | − |
| Melezitose | − | + | + |
| Raffinose | − | + | − |
| Starch | − | − | − |
| Glycogen | − | − | − |
| Xylitol | − | − | − |
| Gentiobiose | W | w | w |
| Turanose | − | + | + |
| Lyxose | − | − | − |
| Tagatose | − | − | − |
| D-Fucose | − | − | − |
| L-Fucose | − | − | − |
| D-Arabitol | − | − | − |
| L-Arabitol | − | − | − |
| Gluconate | W | w | w |
| 2-keto-glugonate | − | − | − |
| 5-keto-gluconate | − | − | − |

(+: positive, w: weak positive, −: negative)

With reference to Table 1, in the sugar fermentation pattern based on the APIWEB database provided by BioMerieux, K2 exhibited 52% similarity to *Lactobacillus plantarum* group 1, K6 exhibited 99.4% similarity to *Lactobacillus plantarum* group 1, and K8 exhibited 99.5% similarity to *Lactobacillus plantarum* group 1. As for the distinctive sugar fermentation characteristics, K2 and K8 strains did not degrade L-arabinose, whereas K6 appeared dark green, thus indicating low fermentation efficiency (w, weak). K2 did not ferment melezitose or raffinose, K6 fermented both melezitose and raffinose, and K8 fermented only melezitose. The turanose fermentation capacity was manifested in K6 and K8. Based on these results, the differences between the three types of strains for the sugar fermentation pattern were confirmed.

Example 2-3. Confirmation of Heat Resistance

In order to investigate the heat resistance of lactic-acid bacteria of the present disclosure, samples were obtained at 20 sec, 40 sec, 60 sec, and 80 sec while bathing at 70° C. in a water bath, a viable cell count was taken to thus determine resistance to heat, and the results thereof are shown in Table 2 below and in FIG. 2. In Table 2 and in FIG. 2, a viable cell count is represented as a $Log_{10}$ CFU/ml value, and the number in parentheses represents the viability (%) compared to the initial count. Each result value is the average of three independent experiments.

TABLE 2

| Strains | Initial | 20 sec | 40 sec | 60 sec |
|---|---|---|---|---|
| Lb. plantarum ATG-K2 | 8.95 ± 0.03 (100.00 ± 8.22%) | 8.99 ± 0.04 (109.65 ± 9.82%) | 8.92 ± 0.03 (91.33 ± 3.50%) | 8.80 ± 0.03 (70.95 ± 6.05%) |
| Lb. plantarum ATG-K6 | 9.44 ± 0.04 (100.00 ± 9.86%) | 9.43 ± 0.04 (97.27 ± 8.70%) | 9.38 ± 0.05 (87.46 ± 9.76%) | 9.28 ± 0.03 (68.88 ± 5.23%) |
| Lb. plantarum ATG-K8 | 9.55 ± 0.03 (100.00 ± 4.23%) | 9.49 ± 0.05 (89.67 ± 8.71%) | 9.41 ± 0.05 (75.26 ± 6.99%) | 9.41 ± 0.05 (74.32 ± 7.74%) |

As is apparent from Table 2 and FIG. 2, K8, which has a viability of 74.32% upon heat treatment for 60 sec, exhibited the highest heat resistance, and the next-highest heat resistance was that of K6, having a viability of 68.88%, followed by K2, having a viability of 70.95%. Here, the maximum bacteria concentration capable of growing in the MRS broth for each culture experiment was about $5 \times 10^8$ CFU/ml for K2, about $3 \times 10^9$ CFU/ml for K6, and about $3 \times 10^9$ CFU/ml for K8.

Example 2-4. Confirmation of Hemolysis of Lactic-Acid Bacteria

In order to evaluate the presence or absence of hemolysis of lactic-acid bacteria in relation to safety of probiotics, K2, K6 and K8 strains were inoculated into a tryptic soybean agar (TSA, Difco Laboratories, USA) containing 5% sheep blood, and were then cultured at 37° C. for about 24 to 48 hr.

As a result, as shown in FIG. 3A, there was growth of lactic-acid bacteria K2, K6 and K8, but hemolysis and clear zones due thereto were not observed.

Example 2-5. Confirmation of Biogenic Amine Production by Lactic-Acid Bacteria

Whether or not biogenic amines such as histamine, tyramine, putrescine or cadaverine, which may be harmful to the human body, were produced was tested in accordance with the method suggested by Bover-Cid and Holzapfel (1999). Briefly, after preparing a medium using the components of the test solid medium suggested by Bover-Cid and Holzapfel (1999), each lactic-acid bacteria strain was inoculated and cultured at 37° C. for about 72 hr, and the color change of the medium was observed. If a biogenic amine is present, the pH value around the inoculated bacteria increases due to the action of decarboxylase, and the bromocresol purple reagent contained in the medium turns from yellow to purple.

As a result, as shown in FIG. 3B, there was growth of K2, K6 and K8 even in the solid medium for observing whether or not biogenic amine was synthesized, but there was no color change, indicating that any one biogenic amine among histidine, tyramine, putrescine, and cadaverine was not produced.

Example 2-6. Antibiotic Test

The antibiotic test was performed using E-test strips (BioMerieux, France) of nine types of antibiotics including ampicillin, vancomycin, gentamicin, kanamycin, streptomycin, clindamycin, erythromycin, tetracycline, and chloramphenicol to determine the minimum inhibitory concentration (MIC). Briefly, lactic-acid bacteria to be tested were each suspended to an absorbance $OD_{600}$ of about 0.8 and were then spread on an MRS solid medium using a sterile cotton swab. The solid medium on which the lactic-acid bacteria were spread was dried for about 3 min, and the E-test strip was placed thereon, followed by culture at 37° C. for 48 hr. Here, due to the nature of lactic-acid bacteria, intrinsic resistance to gentamicin, kanamycin and streptomycin, which are aminoglycosides, may occur, and thus, as a test medium for the corresponding antibiotics, a plate-count agar (PCA, Difco Laboratories, USA) or a Mueller-Hinton agar (MHA, Difco Laboratories, USA) was used. For the types of antibiotics and the criteria for the minimum inhibitory concentration that can be considered safe, reference was made to guidelines published by the European Food Safety Authority (EFSA) (EFSA Panel on Additives and Products or Substances used in Animal Feed, 2012). The results of the above experiments are shown in Table 3 below.

TABLE 3

| Strains | AMP | VAN | GEN | KAN | STR | CD | ERY | TET | CM |
|---|---|---|---|---|---|---|---|---|---|
| Lb. plantarum ATG-K2 | 0.094 | NR | 12 | 12 | NR | 1 | 0.25 | 6 | 4 |
| Lb. plantarum ATG-K6 | 0.094 | NR | 12 | 16 | NR | 0.75 | 0.125 | 3 | 2 |
| Lb. plantarum ATG-K8 | 0.125 | NR | 16 | 16 | NR | 1 | 0.19 | 4 | 0.75 |

The unit of each numerical value in Table 3 is µg/ml, and each abbreviation is as follows: AMP, ampicillin; VAN, vancomycin; GEN, gentamicin; KAN, kanamycin; STR, Streptomycin; CD, clindamycin; ERY, erythromycin; TET, tetracycline; CM, chloramphenicol; NR, not required.

As is apparent from Table 3, all of the three types of Lactobacillus plantarum strains of the present disclosure met the criteria of the guidelines suggested by EFSA and were thus determined to be safe. Here, the minimum inhibitory concentration was 94-128 µg/ml for VAN and 94-194 µg/ml for STR, but the species Lactobacillus plantarum did not require sensitivity values for VAN and STR based on EFSA, which was represented as NR (not required).

Example 2-7. Confirmation of Antimicrobial Effect of Lactic-Acid Bacteria

In order to confirm the antimicrobial functionality of K2, K6 and K8, the antimicrobial activity of lactic-acid bacteria K2, K6 and K8 against a total of seven types of infectious or opportunistic bacteria, including four types of gram-positive SA, LM, SM, and SS and three types of gram-negative EC, PA, and CS, was determined by measuring clear zones through a disc test. Seven types of bacteria cultured overnight in a BHI plate medium were each suspended in 1× phosphate-buffered saline (PBS) until $OD_{600}$ of about 0.8 was obtained. Each suspension was absorbed with a sterile cotton swab, spread over an agar medium for an antimicrobial activity test for lactic-acid bacteria, in which BHI and MRS were mixed at a ratio of 1:1, and dried for about 3 min. Each 8 mm paper disc (Advantec, Japan) was attached to the dried test agar medium, and 35 µl of each of K2, K6, and K8 solutions cultured in an MRS broth for about 18 to 20 hr was inoculated to the paper disc, dried for about 3 min, cultured at 37° C. and observed. The size of the clear zone formed after culture was determined in a manner in which the diameter thereof was measured and was calculated after subtracting 8 mm, which is the diameter of the paper disc.

Based on the results of measurement of the antimicrobial activity of K2, K6 and K8 against seven types of infectious or opportunistic bacteria, the antimicrobial effects of all the lactic-acid bacteria, tested four times on seven types of target bacteria, were represented as the average value, and the results thereof are shown in Table 4 below, indicating that all strains had antimicrobial effects.

TABLE 4

| Strains | SA | TV | SM | SS | EC | PA | CS |
|---|---|---|---|---|---|---|---|
| Lb. plantarum ATG-K2 | 5.00 ± 0.18 | 5.50 ± 0.18 | 4.75 ± 0.28 | 4.13 ± 0.11 | 3.38 ± 0.21 | 3.75 ± 0.13 | 6.50 ± 0.18 |
| Lb. plantarum ATG-K6 | 4.88 ± 0.21 | 4.75 ± 0.13 | 4.13 ± 0.11 | 3.13 ± 0.11 | 3.50 ± 0.18 | 4.00 ± 0.18 | 6.13 ± 0.11 |
| Lb. plantarum ATG-K8 | 4.25 ± 0.13 | 5.18 ± 0.21 | 3.88 ± 0.11 | 4.00 ± 0.18 | 3.50 ± 0.18 | 3.88 ± 0.11 | 5.88 ± 0.11 |

The unit for the diameter of the clear zone, which is each numerical value in Table 4, is mm, and each abbreviation is as follows: *Staphylococcus aureus* KCTC1621 (SA), *Listeria monocytogenes* KCTC3569 (LM), *Streptococcus mutans* KCTC3065 (SM), *Streptococcus salivarius* ATG-P1 (SS), *Escherichia coli* KCTC1682 (EC), *Pseudomonas aeruginosa* KCTC2004 (PA), *Cronobacter sakazakii* KCTC2949 (CS).

Through such experiments, the stability of K2, K6 and K8 can be confirmed through the absence of hemolysis, the absence of biogenic amine causative of allergy or disease, and the safety related to antibiotic sensitivity, and in consideration of the safety of the genus *Lactobacillus plantarum* based on common knowledge (de Varies et al., 2006), it can be found that the lactic-acid bacteria of the present disclosure are safe for application to humans.

Example 2-8. Confirmation of Bile Salt Hydrolase (BSH) Activity

In order to confirm the presence or absence of bile salt hydrolase (BSH) activity as the function of each of the lactic-acid bacteria, an experiment was performed in accordance with the method described in Dashkevicz and Feighner (1989). Briefly, an agar medium was prepared by adding 0.5% (w/v) sodium taurocholic acid (TDCA, Sigma-Aldrich, Germany) to MRS. K2, K6 and K8 lactic-acid bacteria were inoculated into the corresponding agar medium, placed in an anaerobic jar, and cultured at 37° C. for about 72 hr, and the results thereof were confirmed.

As shown in FIG. 4A, all of the K2, K6 and K8 lactic-acid bacteria exhibited BSH activity, and the formation of an opaque white hard colony without sediment infiltrating into the periphery, which is a characteristic phenomenon of *Lactobacillus plantarum* having BSH activity, was observed.

Example 2-9. Confirmation of Ability to Produce Hydrogen Peroxide

For the ability to produce hydrogen peroxide as the function of each of the lactic-acid bacteria, an agar medium was prepared by adding 0.25 mg/ml of tetramethylbenzidine (Sigma-Aldrich, Germany) and 0.01 mg/ml to MRS (McGroarty et al., 1992). Here, the additives were added at about 50° C. after autoclaving of the MRS agar. Each of the lactic-acid bacteria was inoculated into the completely hardened test agar medium, placed in an anaerobic jar, and cultured at 37° C. for about 48-72 hr. After culture, the lactic-acid bacteria were taken out of the anaerobic jar and exposed to air, and the colony and the surrounding color change were observed.

As shown in FIG. 4B, as for the ability to produce hydrogen peroxide, the colony of each of the lactic-acid bacteria and the surface adjacent thereto turned dark blue, indicating that the lactic-acid bacteria K2, K6 and K8 produced hydrogen peroxide.

Example 2-10. Confirmation of Antioxidant Activity

In order to evaluate the antioxidant activity of each of the lactic-acid bacteria strains, a radical-scavenging experiment was conducted using 2,2'-azino-bis(3-ethylbenzthiazoline-6-sulfonic acid) (ABTS, Sigma-Aldrich, Germany). Briefly, lactic-acid bacteria were cultured for about 24 hr, allowed to react with lysozyme (Sigma-Aldrich, Germany) for 2 hr at 37° C., and lysed through sonication to obtain each lactic-acid bacteria lysate. The solid content thereof was measured using a water content analyzer, and a stock solution was adjusted to a concentration of 50 mg/ml. To prepare ABTS, 14 mM ABTS stock solution and 4.9 mM potassium persulfate were mixed at a volume ratio of 1:1, followed by dark reaction overnight so that the resulting mixture turned blue-green. A working solution obtained by diluting the corresponding solution until an absorbance $OD_{734}$ reached about 0.7 was added with 10% of each lactic-acid bacteria lysate sample, followed by dark reaction for 10 min, after which the absorbance at a wavelength of 734 nm was measured, and each measured value was substituted into the following equation.

ABTS radical-scavenging activity (%)= $\{1-(OD_{sample}/OD_{control})\} \times 100$ The experimental results using ABTS are shown in FIG. 4C, and all of the K2, K6 and K8 strains exhibited radical-scavenging activity. Among these strains, K6 exhibited the greatest effect at 10 mg and above, and the next-greatest antioxidant activity was that of K8, followed by K2.

Even through these experimental results, BSH is involved in secondary bile salt metabolism, and thus, when the strains of the present disclosure are developed as products in a form able to ingest lactic-acid bacteria having BSH activity, it can be confirmed that the lactic-acid bacteria have bile resistance and are involved in the intermediate process of cholesterol metabolism of the host, thereby lowering the cholesterol of the host (Begley et al., 2006).

Moreover, the ability of the lactic-acid bacteria of the present disclosure to produce hydrogen peroxide suggests that it can inhibit the proliferation of vaginitis pathogens and opportunistic bacteria by helping antimicrobial activity. Also, it can be confirmed that, through the antioxidant effect of the lysate thereof, excess radicals generated in the affected area can be scavenged, thus having a positive effect on the recovery of the affected area.

Example 3. Confirmation of Antimicrobial Effect of Lactic-Acid Bacteria Against Vaginitis Pathogen Example 3-1. Confirmation of Growth of Lactic-Acid Bacteria Culture Solution In order to measure the activity of the lactic-acid bacteria culture solution on inhibiting the growth of vaginitis pathogens, a 10-fold-concentrated cell-free culture supernatant (CFCS) was prepared. The culture solution of each of K2, K6 and K8 lactic-acid bacteria was centrifuged at 4,000 rpm for 25 min, thereby separating the cells of the lactic-acid bacteria and the culture supernatant from each other. The culture supernatant was filtered using a 0.2 μm pore syringe filter (Sartorius, Germany). The filtered culture supernatant was lyophilized and suspended in 1×PBS to afford a solution concentrated 10-fold compared to the volume of the initial culture solution. CA was inoculated at a concentration of $1 \times 10^5$ CFU/ml and GV was inoculated at a concentration of $1 \times 10^6$ CFU/ml under individual culture conditions. The CFCS of lactic-acid bacteria was added in a volume corresponding to 0.1 times the final volume to the vaginitis-pathogen-inoculated solution so as to reach 1×, and the test group not added with CFCS was used as a control. The mixed composition was cultured for 24 hr for CA and 48 hr for GV under individual vaginitis-pathogen culture conditions, and the absorbance was measured at a wavelength of $OD_{600}$. Based on the measured absorbance, growth inhibition was determined using the following cytotoxicity calculation equation. In this equation, $OD_{control}$ represents the absorbance of the control, and $OD_{cfcs}$ represents the absorbance of the CFCS-added group.

Growth inhibition (%)=$(OD_{control}-OD_{cfcs})/OD_{control} \times 100$

As a result of treating the culture solution inoculated with each vaginitis pathogen with the CFCS of each of the lactic-acid bacteria at a 1× concentration, as shown in FIGS. 5A and 5B, after culture for 24 hr for CA, K2 exhibited growth inhibition of 87.05%, K6 exhibited growth inhibition of 82.11%, and K8 exhibited growth inhibition of 81.34%, and after culture for 48 hr for GV, K2 exhibited growth inhibition of 37.49%, K6 exhibited growth inhibition of 28.25%, and K8 exhibited growth inhibition of 44.60%.

** *Candida albicans* KCTC7678 (CA), *Gardnerella vaginalis* KCTC5096 (GV).

Example 3-2. Confirmation of Coaggregation

As another indicator of antimicrobial activity, the coaggregation of lactic-acid bacteria on the vaginitis pathogen was measured in accordance with the method suggested by Handley et al, 1987.

Briefly, lactic-acid bacteria and vaginitis pathogens were centrifuged at 13,000 rpm for 5 min and the supernatant was decanted, after which the precipitated microorganism cells were washed using 1×PBS. After washing was repeated twice, the microorganisms were each suspended using 1×PBS until an absorbance $OD_{600}$ of 1.0 was obtained. The lactic-acid bacteria suspension and the vaginitis pathogens were mixed at the same volume ratio, homogenized through vortexing, and allowed to stand, after which the supernatant of the mixed solution was carefully obtained at 1, 4, and 8 hr, and the absorbance thereof was measured. The suspension without mixing the microorganisms was used as a control. Based on the measured absorbance, coaggregation was calculated using the following equation. Here, $OD_{patho}$ represents the absorbance of the vaginitis pathogen, $OD_{LAB}$ represents the absorbance of the lactic-acid bacteria, and $OD_{mix}$ represents the absorbance of the mixed solution of microorganisms.

Coaggregation (%)=$\{(OD_{patho}+OD_{LAB})/2-OD_{mix}\}/(OD_{patho}+OD_{LAB})/2$ Based on the results of evaluation of the coaggregation of the lactic-acid bacteria and the vaginitis pathogens as described above, as shown in FIGS. 5C and 5D, for CA at 8 hr, K2 exhibited coaggregation of 70.73%, K6 exhibited coaggregation of 58.57%, and K8 exhibited coaggregation of 57.88%, and for GV, K2 exhibited coaggregation of 32.72%, K6 exhibited coaggregation of 30.39%, and K8 exhibited coaggregation of 20.45%.

** *Candida albicans* KCTC7678 (CA), *Gardnerella vaginalis* KCTC5096 (GV).

Through these experimental results, effects of growth inhibition, coaggregation, and disinfection on CA and GV, which are the main causes of infectious vaginitis, were exhibited. Furthermore, through qualitative antimicrobial activity against seven types of opportunistic bacteria, it was found that the strains of the present disclosure are very effective at balancing vaginal microbiota and preventing infection. In particular, it can be confirmed that the material discharged out of the cells of the lactic-acid bacteria has an antimicrobial effect based on the growth inhibition of CA and GV by the K6 and K8 culture solutions, and also that the strains of the present disclosure can maximize the disinfection power and growth inhibitory effect through close contact with the corresponding pathogens based on the coaggregation ability.

Example 3-3. Confirmation of Disinfection Power Through Coculture

The anti-vaginitis effect of the lactic-acid bacteria of the present disclosure was tested for disinfection power on the vaginitis pathogen through coculture. In the anti-CA experiment, CA at a concentration of about $2.5 \times 10^6$ CFU/ml and each of lactic-acid bacteria at a concentration of about $2.5 \times 10^6$ CFU/ml were mixed at a ratio of 1:1, and coculture thereof was carried out in a culture medium of YM and MRS mixed at 1:1. In the anti-GV experiment, GV at a concentration of about $1.0\times10^8$ CFU/ml and each of lactic-acid bacteria at a concentration of about $1.0\times10^8$ CFU/ml were mixed at a ratio of 1:1 and then inoculated into a 10% horse-serum BHI broth. Each coculture experiment was conducted for 48 hr, and portions of the samples were collected initially and every 24 hr, and a viable cell count was taken through a serial dilution method and a plate-spreading method. In the anti-CA experiment, in order to measure CA alone, a YM plate medium containing ampicillin at a concentration of 100 µg/ml was used. In the anti-GV experiment, CFU was measured by distinguishing the colony forms between GV and lactic-acid bacteria using a 5% rabbit blood BHI plate medium.

In the coculture experiments of the lactic-acid bacteria and the vaginitis pathogens for 48 hr, as shown in FIGS. 6A and 6B, in the experimental groups in which K2, K6 and K8 were cocultured with CA, CA completely disappeared at 48 hr, and disinfection power at 24 hr was 99.03% in K2, 99.49% in K6, and 99.53% in K8.

In the experiment for GV, as shown in FIGS. 6C and 6D, disinfection power at 24 hr was 87.37% in K2, 92.50% in K6, and 93.71% in K8. Here, GV died at an average of about 90% after the initial 24 hr and then grew slowly, which is presumed to be due to a biofilm created for self-protection, which is one of the characteristics of GV. In the coculture experiments for CA and GV, it was confirmed that the disinfection values at 24 hr and at 48 hr were statistically significant compared to the initial value (OH) of each vaginitis pathogen.

Example 4. Vaginal Health Improvement Effect of Lactic-Acid Bacteria

Example 4-1. Effect of Lactic-Acid Bacteria on Enhancing Innate Immunity

In order to measure the immunological effects of K2, K6 and K8 lactic-acid bacteria, a cytokine quantification experiment using cells was performed. The cells that were used were a mouse macrophage cell line RAW264.7, and the medium used for each cell experiment was a Gibco® Dulbecco's Modified Eagle Medium (DMEM, Gibco, USA) supplemented with 10% fetal bovine serum (Gibco, USA) and 1% penicillin/streptomycin cocktail (Sigma-Aldrich, Germany). RAW264.7 cells cultured at about 80-90% confluency before material treatment were recovered and seeded in an amount of $1\times10^6$ cells per well of a 24-well plate. After seeding, culture was carried out in an environment of 37° C. and 5% $CO_2$ for 24 hr in order to realize attachment to the 24-well plate and stabilization thereof. Each well was treated with the lactic-acid bacteria lysate at concentrations of 100 µg/ml and 500 µg/ml, and 1 µg/ml of lipopolysaccharide (LPS, Sigma-Aldrich, Germany) was used as a positive control, and an experimental group not treated with any material was used as a negative control. The cells were cultured at 37° C. and 5% $CO_2$ for 24 hr after material treatment, and the cell culture solution was recovered, followed by enzyme-linked immunosorbent assay (ELISA) for IL-6 and TNF-α. Measurement was performed for IL-6 using a Mouse IL-6 Quantikine ELISA Kit (R&D systems, USA) and for TNF-α using a Mouse TNF-alpha Quantikine ELISA Kit (R&D systems, USA).

As a result, as shown in FIGS. 7A and 7B, when RAW264.7 cells were treated with the lactic-acid bacteria lysate, the concentrations of IL-6 and TNF-α were increased compared to the control. When using the K8 lysate at a concentration of 500 µg/ml, the amount of IL-6 that was produced was significantly reduced compared to when using the K8 lysate at a concentration of 100 µg/ml, and in the case of the K2 lysate, it was found that the amount of TNF-α that was produced was significantly increased with an increase in the concentration thereof. Overall, the amounts of IL-6 and TNF-α increased in all of the groups treated with the lactic-acid bacteria lysate, and the increase thereof was lower than that of the LPS-treated group.

Example 4-2. Effect of Lactic-Acid Bacteria on Inhibiting Inflammation

An experiment on inflammation inhibition was performed in the same manner as the test method for confirming the increase in innate immunity of Example 4-1, but an experimental group using both the lactic-acid bacteria lysate and LPS was further added. This experiment is intended to measure the ability to inhibit inflammation induced by LPS. To this end, each experimental group was cultured in an environment of 37° C. and 5% $CO_2$ for 24 hr after material treatment, the cell culture solution was recovered, and ELISA for IL-10 was performed using a mouse IL-10 Quantikine ELISA Kit (R&D systems, USA).

As a result, as shown in FIG. 8, when RAW264.7 cells were treated both with 1 µg/ml of LPS and with 100 µg/ml of each lactic-acid bacteria lysate, the concentration of IL-10 was significantly increased.

The groups further treated with the K2 lysate and the K6 lysate exhibited similarly increased IL-10 levels (about 1100-1150 µg/ml), and the group treated with the K8 lysate exhibited a relatively small increase in IL-10 (about 400 µg/ml) compared to the groups treated with the K2 lysate and the K6 lysate. However, compared to the group treated with LPS alone, all experimental groups treated with both lactic-acid bacteria and LPS exhibited a statistically significant increase.

From an immunological point of view, based on these experimental results, IL-6 and TNF-α were induced in the macrophage cell line RAW264.7 by all of the three types of lactic-acid bacteria lysates K2, K6 and K8, which is considered to demonstrate the effect of increasing innate immunity or enhancing immunity. IL-6 is a very important cytokine in immune regulation, having, for example, proinflammatory and anti-inflammatory effects, including activation of macrophages, induction and aggregation of neutrophils, and inflammatory response activity against invading pathogens (Scheller et al., 2001; Fielding et al., 2008). It is reasonable to consider this effect as an immunity-enhancing effect, rather than a pathological inflammatory response, based on low increase compared to IL-6 and TNF-α induced by LPS, which is a representative inflammatory substance. Moreover, the increased production of TNF-α, which is a cytokine that has effects such as anti-tumor effects, inhibition of fever and viral proliferation, activation of macrophages, and the like, also indicates that the lactic-acid bacteria of the present disclosure have an effect of increasing innate immunity (Vujanovic, 2011). In general, treatment with LPS causes inflammation and IL-10 is produced to control and inhibit the inflammatory response, and the amount of IL-10 that was produced was 2-5 times greater than that of IL-10 induced by LPS, based on which the lactic-acid bacteria are evaluated to be effective at inhibiting excessive inflammatory response.

Therefore, it is concluded that K2, K6 and K8 lactic-acid bacteria are strains that are safe, have antimicrobial activity against vaginitis pathogens, an antioxidant effect, and effects of increasing innate immunity and inhibiting inflammation, ultimately improving the urogenital health of the user.

Example 5. Whole-Genome Analysis of Lactic-Acid Bacteria

For whole-genome analysis of K2, K6 and K8 lactic-acid bacteria, genomic DNA was extracted, and the nucleotide sequence thereof was analyzed using Pacific Bioscience's Single-Molecule Real-Time (SMRT) sequencing technique. The nucleotide sequence data thus obtained was assembled using the Hierarchical Genome Assembly Process (HAGP) 2 protocol of SMRT analysis software v2.3.0, and Rapid Annotation using a Subsystem Technology (RAST) server (hypertext transfer protocol: rast.nmpdr.org/) was utilized for annotation. In addition, Average Nucleotide Identity (ANI) analysis was conducted in order to confirm the independence of three types of lactic-acid bacteria, and safety was verified once more from genetic information using PathoFinder 1.1 (hypertext transfer protocol: cge.cbs.dtu.dk/services/PathogenFinder/).

Based on the results of analyzing the whole genome of lactic-acid bacteria K2, K6 and K8, as is apparent from Tables 5 and 6 below, chromosomal DNA sizes thereof were different, and the number and size of plasmids were also different.

In ANI analysis conducted to confirm the independence of the three types of lactic-acid bacteria, K2 and K6 exhibited identity of 96.25%, K2 and K8 exhibited identity of 96.09%, and K6 and K8 exhibited identity of 99.92%, indicating that these belonged to the species *Lactobacillus plantarum*, but there was a difference of 0.08 to 3.91% therebetween.

TABLE 5

| Strains | Lb. plantarum ATG-K2 | Lb. plantarum ATG-K6 | Lb. plantarum ATG-K8 |
|---|---|---|---|
| Chromosome (bp) | 3,034,884 | 3,205,672 | 3,221,272 |
| Plasmid 1 (bp) | 61,159 | 56,833 | 54,492 |
| Plasmid 2 (bp) | 40,101 | — | — |
| Plasmid 3 (bp) | 38,954 | — | — |

TABLE 6

Results of whole-genome analysis of each of *Lactobacillus plantarum* K2, K6 and K8 strains

| Attribute | ATG-K2 | ATG-K6 | ATG-K8 |
|---|---|---|---|
| Total genome size (bp) | 3,175,098 | 3,262,505 | 3,275,764 |
| Chromosome size | 3,034,884 | 3,205,672 | 3,221,272 |
| Plasmid number | 3 | 1 | 1 |
| DNA G + C(%) | 45.19 | 44.54 | 44.54 |
| Total genes | 3,114 | 3,178 | 3,186 |
| Protein coding genes | 2,857 | 2,999 | 2,999 |
| rRNA genes | 16 | 16 | 16 |
| tRNA genes | 65 | 67 | 67 |
| ncRNA genes | 4 | 4 | 4 |
| Pseudo genes | 172 | 92 | 100 |
| GenBank accession | GCA_003597635.1 | GCA_003597595.1 | GCA_003597615.1 |

Thereafter, based on the results of annotation through the RAST server using the genome information described above, it was confirmed that the gene compositions of individual strains were also different, as shown in Table 7 below. The K2 lactic-acid bacteria had 49 genes associated with the cell wall and capsule, whereas the K6 and K8 lactic-acid bacteria had 71 genes. In the case of genes associated with carbohydrates, the K2 lactic-acid bacteria had 215 genes, the K6 lactic-acid bacteria had 235 genes, and the K8 lactic-acid bacteria had 245 genes. The difference therebetween appears to be that the three types of lactic-acid bacteria belong to the same species but exhibit different growth rates or functions.

TABLE 7

Gene composition of each of *Lactobacillus plantarum* K2, K6 and K8 strains

| Target gene | ATG-K2 | G-K6 | G-K8 |
|---|---|---|---|
| Cofactors, Vitamins, Prosthetic Groups, Pigments | 103 | 117 | 102 |
| Cell Wall and Capsule | 49 | 71 | 71 |
| Virulence, Disease and Defense | 42 | 39 | 39 |
| Potassium Metabolism | 6 | 5 | 5 |
| Photosynthesis | 0 | 0 | 0 |
| Miscellaneous | 18 | 18 | 18 |
| Phages, Prophages, Transposable Elements, Plasmids | 10 | 11 | 11 |
| Membrane Transport | 55 | 48 | 48 |
| Iron Acquisition and Metabolism | 5 | 5 | 5 |
| RNA Metabolism | 41 | 39 | 39 |
| Nucleosides and Nucleotides | 88 | 88 | 89 |
| Protein Metabolism | 146 | 148 | 148 |
| Cell Division and Cell Cycle | 4 | 4 | 4 |
| Motility and Chemotaxis | 0 | 0 | 0 |
| Regulation and Cell Signaling | 34 | 27 | 29 |
| Secondary Metabolism | 4 | 4 | 4 |
| DMA Metabolism. | 58 | 55 | 55 |
| Fatty Acids, Lipids, and Isoprenoids | 36 | 35 | 37 |
| Nitrogen Metabolism | 0 | 0 | 0 |
| Dormancy and Sporulation | 6 | 6 | 6 |
| Respiration | 17 | 15 | 16 |
| Stress Response | 19 | 21 | 21 |
| Metabolism of Aromatic Compounds | 5 | 8 | 8 |
| Amino Acids and Derivatives | 196 | 189 | 190 |
| Sulfur Metabolism | 3 | 3 | 3 |
| Phosphorus Metabolism | 35 | 33 | 33 |
| Carbohydrates | 215 | 235 | 246 |
| Total identified gene percentage in RAST server subsystem database | 29% | 26% | 28% |

Formulation Example 1. Pharmaceutical Formulation

Formulation Example 1-1. Preparation of Tablet 200 g of any one of *Lactobacillus plantarum* K2, K6 and K8 of the present disclosure was mixed with 175.9 g of lactose, 180 g of potato starch and 32 g of colloidal silicic acid. The resulting mixture was added with a 10% gelatin solution, pulverized, and passed through a 14-mesh sieve. The resulting product was dried and added with 160 g of potato starch, 50 g of talc and 5 g of magnesium stearate, and the resulting mixture was manufactured into tablets.

Formulation Example 2. Preparation of Food

Formulation Example 2-1. Preparation of Cooking Seasoning

A cooking seasoning for health improvement was manufactured by adding 1 wt % of any one of the *Lactobacillus plantarum* K2, K6 and K8 lactic-acid bacteria of the present disclosure to a cooking seasoning.

Formulation Example 2-2. Preparation of Dairy Products

Various dairy products such as butter and ice cream were manufactured using milk containing 0.1 wt % of any one of the *Lactobacillus plantarum* K2, K6 and K8 lactic-acid bacteria of the present disclosure.

Formulation Example 2-5. Preparation of Vegetable Juice

A vegetable juice for health improvement was manufactured by adding 0.5 g of any one of the *Lactobacillus plantarum* K2, K6 and K8 lactic-acid bacteria of the present disclosure to 1,000 ml of tomato juice or carrot juice.

Formulation Example 2-6. Preparation of Fruit Juice

A fruit juice for health improvement was manufactured by adding 0.1 g of any one of the *Lactobacillus plantarum* K2, K6 and K8 lactic-acid bacteria of the present disclosure to 1,000 ml of apple juice or grape juice.

[Depositary Authority]
Name of Depositary Authority: Korean Collection for Type Cultures
Accession number: KCTC13577BP
Accession date: 20180710
Name of Depositary Authority: Korean Collection for Type Cultures
Accession number: KCTC13570BP
Accession date: 20180703
Name of Depositary Authority: Korean Collection for Type Cultures
Accession number: KCTC13571BP
Accession date: 20180703

---

The invention claimed is:

1. A method of preventing or treating vaginitis in a mammalian subject in need thereof comprising administering to the subject a composition comprising an amount of the isolated *Lactobacillus plantarum* ATG-K2 strain having the accession number KCTC 13577BP and comprising the 16S rRNA nucleotide sequence of SEQ ID NO: 1.

2. The method of claim 1, wherein the *Lactobacillus plantarum* ATG-K2 strain has antimicrobial activity against at least one vaginitis pathogen selected from the group consisting of *Candida albicans* and *Gardnerella vaginalis*.

3. The method of claim 1, wherein the *Lactobacillus plantarum* ATG-K2 strain has antimicrobial activity against at least one bacterium selected from the group consisting of *Staphylococcus aureus, Listeria monocytogenes, Streptococcus mutans, Streptococcus salivarius, Escherichia coli, Pseudomonas aeruginosa*, and *Cronobacter sakazakii*.

4. The method of claim 1, wherein the *Lactobacillus plantarum* ATG-K2 strain does not cause hemolysis and does not produce histamine, tyramine, putrescine, and cadaverine.

5. The method of claim 1, wherein the *Lactobacillus plantarum* ATG-K2 strain has bile salt hydrolase activity, ability to produce hydrogen peroxide, or antioxidant activity.

6. The method of claim 1, wherein the *Lactobacillus plantarum* ATG-K2 strain is not resistant to ampicillin, vancomycin, gentamicin, kanamycin, streptomycin, clindamycin, erythromycin, tetracycline, and chloramphenicol.

7. The method of claim 1, wherein the administering of the composition increases an amount of interleukin-6 (IL-6), tumor necrosis factor-alpha (TNF-alpha), and interleukin-10 (IL-10) in the subject compared to a corresponding subject not administered with the composition.

* * * * *